(12) United States Patent
Prasad

(10) Patent No.: US 12,226,443 B2
(45) Date of Patent: Feb. 18, 2025

(54) POLYPHENOL COMPOSITION AND METHOD OF ITS USE AND MANUFACTURE IN THE TREATMENT OF METABOLIC DISORDERS

(71) Applicant: Vidya Herbs, Inc., Fullerton, CA (US)

(72) Inventor: Kodimule Shyam Prasad, Bangalore (IN)

(73) Assignee: Vidya Herbs, Inc., Red Bank, NJ (US)

( * ) Notice: Subject to any disclaimer, the term of this patent is extended or adjusted under 35 U.S.C. 154(b) by 0 days.

(21) Appl. No.: 16/247,464

(22) Filed: Jan. 14, 2019

(65) Prior Publication Data

US 2019/0216875 A1 Jul. 18, 2019

Related U.S. Application Data

(60) Provisional application No. 62/641,421, filed on Mar. 12, 2018, provisional application No. 62/617,585, filed on Jan. 15, 2018.

(51) Int. Cl.
*A61K 36/738* (2006.01)
*A61P 3/00* (2006.01)
*A61P 39/06* (2006.01)

(52) U.S. Cl.
CPC .............. *A61K 36/738* (2013.01); *A61P 3/00* (2018.01); *A61P 39/06* (2018.01)

(58) Field of Classification Search
CPC .................................................. A61K 36/738
See application file for complete search history.

(56) References Cited

U.S. PATENT DOCUMENTS

| | | | |
|---|---|---|---|
| 10,369,179 B2 | 8/2019 | Prasad |
| 10,646,527 B2 | 5/2020 | Prasad |

FOREIGN PATENT DOCUMENTS

| | | | |
|---|---|---|---|
| CN | 101664518 A | * | 3/2010 |
| JP | 2009102288 A | * | 5/2009 |
| JP | 2010006748 A | * | 1/2010 |

OTHER PUBLICATIONS

NIH: National Institute on Aging. Healthy Eating: Maintaining a Healthy weight. Retrieved from the Internet on: Nov. 17, 2021. Retrieved from: <URL: https://www.nia.nih.gov/health/maintaining-healthy-weight>. 3 pages. (Year: 2021).*
NIH: Treatment for Overweight & Obesity. Retrieved from the Internet on: Nov. 17, 2021. Retrieved from: <URL: https://www.niddk.nih.gov/health-information/weight-management/adult-overweight-obesity/treatment>. 5 pages. (Year: 2021).*
Nagao, A Catechin-rich Beverage Improves Obesity and Glucose In Patients with Type 2 Diabetes, Obesity (2008) 17, 310-317.
Bhardwaj, Catechin Averts Experimental Diabetes Mellitus-Induced Vascular Endothelial Structural and Functional Abnormalities, Cardiovascular Toxicol. (2014) 14:41-51.
Hussain, Quercetin Postrandial Hyperglycemia In Type 2 Diabetic Challenged with Carbohydrates Load, International Journal of Diabetes Research 2012, 1(3): 32-35.
Aguirre, Beneficial Effects of Quercetin on Obesity and Diabetes, The Open Nutraceuticals Journal (2011) 4, 189-198.

* cited by examiner

*Primary Examiner* — Terry A McKelvey
*Assistant Examiner* — Catheryne Chen
(74) *Attorney, Agent, or Firm* — TMB Law; Timothy M. Brown

(57) ABSTRACT

The invention provides a polyphenolic composition and method for its use and manufacture in the treatment of metabolic disorders. The active agents of the composition can include flavonoids and anthocyanins. The active agents can be obtained from rose petal extract, including *Rosa multiflora* rose petal extract. The composition finds use in the treatment of obesity and complications associated with obesity.

23 Claims, 16 Drawing Sheets

POLYPHENOL COMPOSITION AND METHOD OF ITS USE AND MANUFACTURE IN THE TREATMENT OF METABOLIC DISORDERS

CROSS-REFERENCE TO RELATED APPLICATIONS

This application claims priority to U.S. Provisional Application No. 62/617,585 filed Jan. 15, 2018 and U.S. Provisional Application No. 62/641,421 filed Mar. 12, 2018, the entire disclosures of which are incorporated by reference herein for all purposes.

FIELD OF INVENTION

The invention generally relates to polyphenol compositions and methods of making and using the same in the treatment of metabolic disorders.

BACKGROUND OF THE INVENTION

Metabolism is the breakdown of complex food into simple biomolecules such as proteins, carbohydrates and fats. Any disturbance in the regulation of metabolism leads to the metabolic disorders which include obesity, type 2 diabetes, dyslipidemia and metabolic syndrome. Increasing incidence of the metabolic disorders in the modern world could be attributed to the change in life style and dietary habits (Joint FAO/WHO Expert consultation, 2003; Popkin, 2001). Obesity is the excess accumulation of adipose tissue; it is one of the most common global health issues affecting both genders. Obesity is associated with other health complications such as diabetes, cardiovascular diseases, pulmonary diseases and non-alcoholic fatty liver disease (World cancer research 2007).

Current medications for obesity include synthetic drugs having different cellular mechanism of action. Orlistat, Lorcaserin, Phentermine are examples of such synthetic drugs (Rucker et al. 2007; Kim et al. 2014). However most of the commercially available synthetic drugs have been associated with side effects such as kidney stones, back pain, headache, fatigue, constipation and even liver injury. Synthetic anti-obesity medications have safety risks such as psychiatric events and weight gain after the cessation of the drug. Hence there is a need for an alternative medical approach to produce effective long-term benefits.

Herbal preparations such as extracts and polyherbal formulations have drawn much attention due to their rich phytochemical profile. Enormous efforts have been made during the last two decades to introduce drugs of herbal origin (Newman and Cragg, 2012). Several active principles from medicinal plants have been studied for efficacy in improving human health and quality of life. Research on medicinal plants has gathered ample information on the health benefits by the aid of preclinical and clinical studies. Several mechanisms of anti-hyperlipidemic, anti-diabetic effects of herbs and their active constituents have been revealed (Wong et al. 2014; Hasani-Ranjbar et al. 2010; Hasani-Ranjbar et al. 2010). Even though the plant derived compounds have a slower rate of therapeutic efficacy as compared to their synthetic counterparts, there are little or no adverse effects following their consumption. Examples of plants with anti-obesity effects are: Garcinia atroviridis, black Chinese tea, Cissus *quadrangularis*, green coffee beans, *Panax* japonicas, pomegranate leaves and Nigella *sativa* (Hasani Ranjbar et al. 2009; Hasani Ranjbar et al. 2013). A proper response to the multifactorial metabolic disorders such as obesity and diabetes is expected by the use of herbal medicine. Accordingly, there exists a need for the development of new agents of natural origin and methods to stimulate lipid lowering effects and promote weight loss and associated complications.

SUMMARY OF THE INVENTION

Owing to the rich polyphenol content and presence of pharmacologically active compounds in rose petal extract, the composition of the present invention is useful for improving the health status during pathological conditions such as obesity and type 2 diabetes. It is an object of the present invention to provide methods for making and using polyphenol compositions obtained from rose petal extract that are effective on inhibiting obesity/weight gain without the side effects associated with synthetic medications.

The present invention provides methods for making therapeutic compositions derived from the petals of *Rosa multiflora* and other red rose varieties. The present invention also provides methods of analysis of phytoconstituents in the composition's bioactive fraction.

Further in accordance with the present invention, there is provided an in silico approach to identify the interactions of phytochemicals in the composition with target proteins of metabolic disorders such as obesity and type 2 diabetes such as AMP activated protein kinase, PPARα, PPARγ and α-glucosidase, using molecular docking.

Still further in accordance with the present invention, there are provided methods for evaluating the inhibitory potential of the composition against key metabolic enzymes, including pancreatic lipase and α-glucosidase.

Further in accordance with the present invention, there are provided methods for evaluating the efficacy of the composition in regulating the adipocyte differentiation, using mammalian cell line 3T3L-1 preadipocytes as in vitro model.

Still further in accordance with the present invention, the composition finds use in attenuating hyperlipidemia associated with obesity and disorders associated with obesity, such as Type-2 diabetes.

DEFINITIONS

Figure 1A:
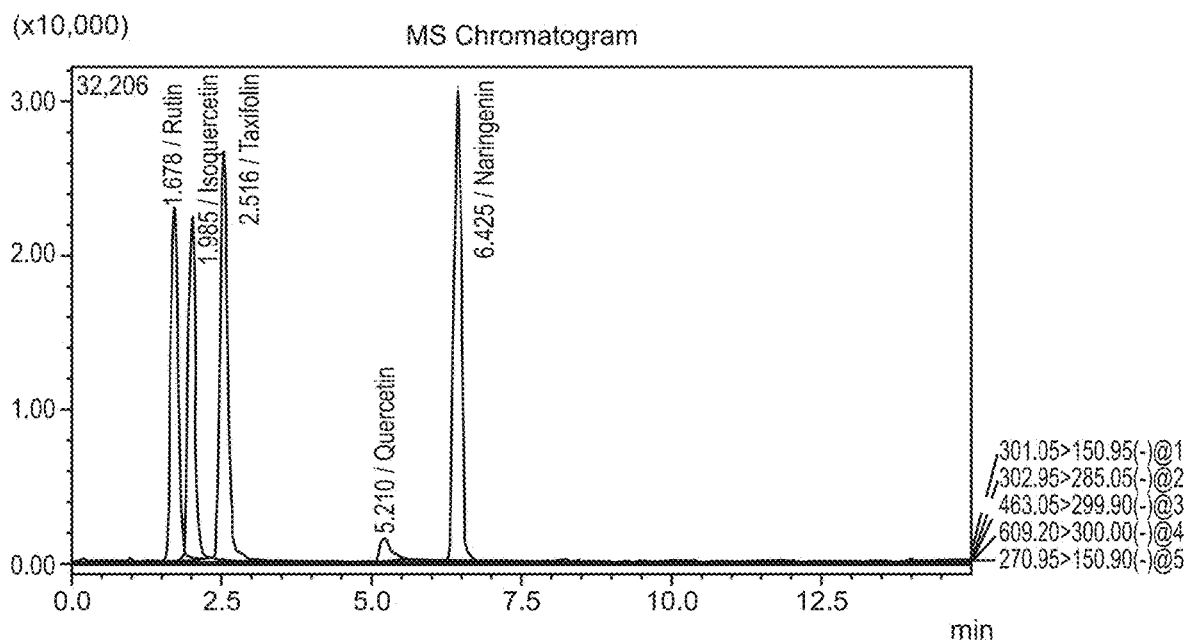
FIGS. 1A and 1B show the LCMS chromatograms of flavonoids present in an embodiment the composition.

As used herein, the term "about" means the quantity, level, value, number, frequency, percentage, dimension, size, amount, weight or length that is referenced or that varies (plus or minus) by as much as 30%, 25%, 20%, 15%, 10%, 9%, 8%, 7%, 6%, 5%, 4%, 3%, 2% or 1% to the referenced quantity, level, value, number, frequency, percentage, dimension, size, amount, weight or length.

As used herein, the term "anthocyanin" refers to the water-soluble vacuolar pigments, or analogues or derivatives thereof, that, depending on their pH, may appear red, purple, or blue. Anthocyanins are a subgroup of flavonoids. Anthocyanins are derived from anthocyanidins by adding sugars. Anthocyanins for use with the invention can be derived from the anthocyanidins apigeninidin, aurantinidin, capensinidin, cyanidin, delphinidin, europinidin, hirsutidin, luteolinidin, malvidin, pelargonidin, peonidin, petunidin, pulchellidin, rosinidin, or triacetidin, or combinations thereof.

As used herein, and unless indicated otherwise, the term "diabetes" includes, but is not limited to, type 1 diabetes, type 2 diabetes, non-insulin dependent diabetes mellitus, and diabetes insipidus. Diabetes can be accompanied by related complications including, for example, obesity, high cholesterol, and hyperlipidemia.

As used herein, the phrases "effective amount," "effective dose," and "therapeutically effective amount," refer to that amount of a therapeutic agent sufficient to ameliorate a disorder. For example, for the given parameter, a therapeutically effective amount will show an increase or decrease of therapeutic effect at least 5%, at least 10%, at least 15%, at least 20%, at least 25%, at least 40%, at least 50%, at least 60%, at least 75%, at least 80%, at least 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "flavonoids" refers to a group of plant metabolites, or analogues or derivatives thereof, that provide health benefits through cell signaling pathways and antioxidant effects. Flavonoids are polyphenolic molecules containing 15 carbon atoms and are soluble in water. Flavonoids are a subgroup within the polyphenols and function as natural antioxidants.

As used herein, the term "hyperglycemia" and the phrase "high blood sugar," refer to a condition in which an excessive amount of glucose (e.g. greater than about a 125 mg/dL fasting plasma glucose level) circulates in the blood plasma.

As used herein, the term "increase" refers to any measurable increase in a parameter relative to control conditions.

As used herein, the phrase "metabolic disorder" includes, but is not limited to, being overweight, obesity, prediabetes, polycystic ovary syndrome, dislipidemia or disorders of lipid metabolism (e.g. hyperlipidemia), hyperglycemic conditions, such as insulin-dependent (type 1) and insulin-independent (type 2) diabetes, pre-diabetes, as well as physiological conditions or disorders associated with or that result from the hyperglycemic condition.

As used herein, the terms "obese" and "obesity" refer to a subject having a body mass index of 30 or higher.

As used herein, the term "polyphenols" refers to a compound containing more than one phenolic hydroxyl group. Polyphenols are a structural class of mainly natural, but also synthetic or semisynthetic organic chemicals characterized by the presence of large multiples of phenol structural units. Polyphenols are a class of colorful phenolic organic compounds found in plants.

As used herein, the term "pre-diabetes" refers to symptoms of diabetes wherein the patient exhibits elevated glucose levels but the full onset of disorders associated with diabetes has not yet manifested itself.

As used herein, the term "reduce" refers to any measurable decrease in a parameter relative to control conditions.

As used herein, the terms "subject," "patient," "individual" and like terms are used interchangeably and refer to, except where indicated, mammals such as humans and non-human primates, as well as livestock and companion and laboratory research animals. The terms can refer to an individual that has been diagnosed with, is currently following a therapeutic regimen for, or is at risk of developing a metabolic disorder (e.g. due to family history, sedentary lifestyle, etc.).

As used herein, the terms "therapy," "treating," "treat," and "treatment" refer to preventing, inhibiting the progression of, reducing the severity of, or the improvement of, a disorder, disease or disease state or the symptoms associated with the disorder, disease or disease state.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

DETAILED DESCRIPTION

The invention generally relates to polyphenol compositions and methods of their use and manufacture in the treatment of metabolic disorders. The compositions can comprise polyphenols, including flavonoids and anthocyanins.

In some aspects, the invention provides a composition comprising polyphenols, flavonoids, anthocyanins, phenolic acids, chlorogenic acids, or combinations thereof. The composition can comprise polyphenols, flavonoids, anthocyanins, phenolic acids, chlorogenic and acids. The composition can consist essentially of polyphenols, flavonoids, anthocyanins, phenolic acids, chlorogenic acids, and combinations thereof. The composition can comprise about 66.0 w/w % polyphenols, about 9.5 w/w % flavonoids, and about 2.7 w/w % anthocyanins. The composition can comprise about 66.0 w/w % total polyphenols, about 9.5 w/w % total flavonoids, and about 2.7 w/w % total anthocyanins. The composition can comprise about 66.0 w/w % polyphenols, wherein the polyphenols comprise about 9.5 w/w % flavonoids, and the flavonoids comprise about 2.7 w/w % anthocyanins. The composition can comprise about 9.5 w/w % flavonoids, wherein the flavonoids comprise about 2.7 w/w % anthocyanins and the extract has a total polyphenol content of about 66.0 w/w % polyphenols. In other aspects, the composition can comprise 66.44±3.09 w/w % polyphenols, 9.47±1.23 w/w % flavonoids, and 2.73±0.38 w/w % anthocyanins. The composition can comprise 66.44±3.09 w/w % total polyphenols, 9.47±1.23 w/w % total flavonoids, and 2.73±0.38 w/w % total anthocyanins. The composition can comprise 66.44±3.09 w/w % polyphenols, wherein the polyphenols comprise 9.47±1.23 w/w % flavonoids, and the flavonoids comprise 2.73±0.38 w/w % anthocyanins. The composition can comprise 9.47±1.23 w/w % flavonoids, wherein the flavonoids comprise 2.73±0.38 w/w % anthocyanins and the extract has a total polyphenol content of 66.44±3.09 w/w % polyphenols. The composition can consist essentially of about 66.0 w/w % total polyphenols, about 9.5 w/w % total flavonoids and about 2.7 w/w % total anthocyanins. The composition can consist essentially of 66.44±3.09 w/w % total polyphenols, 9.47±1.23 w/w % total flavonoids, and 2.73±0.38 w/w % total anthocyanins.

The polyphenols of the composition can comprise flavonoids and non-flavonoid polyphenols. The flavonoids can comprise anthocyanins and non-anthocyanin flavonoids. Non-limiting flavonoids of the composition include, but are not limited to, quercetin, isoquercetin, rutin, taxifolin, myricetin, kaempferol, kaempferol pentoside, quercetin 3-O-xyloside, quercetin 3-O-glucoside, quercetin 3-O-rhamnoside, quercetin 3-O-galactoside, aglycone quercetin, kaempferol deoxyhexoside, kaempferol acetyldisaccharide, kaempferol 3-O-rutinoside, isorhamnetin, luteolin, apigenin, hesperetin, naringenin, eriodictyol, catechins, epigallocatechins, theaflavins, cyaniding, delphinidin, malvidin, pelargonidin, peonidin, petunidin, daidzein, genistein, glycitein, or combinations thereof. The flavonoids can be selected from the group consisting of quercetin, isoquercetin, rutin, taxifolin, myricetin, kaempferol, kaempferol pentoside, quercetin 3-O-xyloside, quercetin 3-O-glucoside, quercetin 3-O-rhamnoside, quercetin 3-O-galactoside, aglycone quercetin, kaempferol deoxyhexoside, kaempferol acetyldisaccharide, kaempferol 3-O-rutinoside, isorhamnetin, luteolin, apigenin, hesperetin, naringenin, eriodictyol, catechins, epigallocatechins, theaflavins, cyaniding, delphinidin, malvidin, pelargonidin, peonidin, petunidin, daidzein, genistein, and glycitein. The composition can comprise the flavonoids disclosed in U.S. Pat. No. 9,839,624, the entire contents of which are incorporated herein by reference for all purposes.

In some aspects, the flavonoids comprise isoquercetin, rutin, quercetin, taxifolin, or combinations thereof. The flavonoids can comprise isoquercetin, rutin, quercetin, and taxifolin. The composition can comprise about 3.5 w/w % isoquercetin, about 0.3 w/w % rutin, about 0.3 w/w % quercetin, about 0.001 w/w % taxifolin, or combinations thereof. The composition can comprise about 3.5 w/w % isoquercetin, about 0.3 w/w % rutin, about 0.3 w/w % quercetin, and about 0.001 w/w % taxifolin. The composition can comprise 3.48±0.11 w/w % isoquercetin, 0.33±0.02 w/w % rutin, 0.25±0.28 w/w % quercetin, 0.001±0.00 w/w % taxifolin, or combinations thereof. The composition can comprise 3.48±0.11 w/w % isoquercetin, 0.33±0.02 w/w % rutin, 0.25±0.28 w/w % quercetin, and 0.001±0.00 w/w % taxifolin.

In some embodiments, the composition comprises quercetin. The quercetin can be quercetin glucosides, including naturally occurring forms of quercetin glycosides. Quercetin glycosides can include rutin, (for example, rutoside, sophorin, and quercetin-3-O-rutinoside). Quercetin glycoside can also include quercitrin, which is a 3-O-a-L-rhamnoside. Quercetin glycoside can also include guaijaverin, which is a 3-O-arabinoside. Quercetin glycoside can also include hyperoside, which is a 3-O-galactoside. Quercetin glycoside can also include isoquercetin, which is a 3-O-glucoside. Quercetin glycoside can also include spiraeoside, which is a 4'-O-glucoside. Quercetin glycoside can also include miquelianin, which is a quercetin 3-O-B-d-glucuronopyranoside.

In some embodiments, quercetin comprises any aglycone quercetin, any quercetin glycoside, and/or any quercetin derivative. Quercetin can be derived from any appropriate plant-based source. Quercetin can comprise any plant-based extract that is enriched in any aglycone quercetin, any quercetin glycoside, and/or any quercetin derivative. Quercetin can be extracted, isolated, and/or enriched by any appropriate methods as known in the art. Quercetin can comprise a mixture further comprising one or more of polyphenols, flavonoids, and/or flavonols.

The composition can comprise anthocyanins. The anthocyanins can comprise cyanidin 3-O-glucoside, cyanidin 3-O-rutinoside, delphinidin 3-O-galactoside, delphinidin 3-O-glucoside, or combinations thereof. The anthocyanins can be selected from the group consisting of cyanidin 3-O-glucoside, cyanidin 3-O-rutinoside, delphinidin 3-O-galactoside, and delphinidin 3-O-glucoside. The anthocyanins can comprise cyanidin 3-O-glucoside, cyanidin 3-O-rutinoside, delphinidin 3-O-galactoside, and delphinidin 3-O-glucoside. The extract can comprise the anthocyanins disclosed in U.S. Pat. No. 9,839,624, the entire contents of which are incorporated herein by reference for all purposes.

The composition can comprise phenolic acids. The phenolic acids can comprise ethyl gallate, ellagic acid, methyl gallate, catechin, gallic acid, 3,4-dihydroxy benzoic acid, or combinations thereof. The phenolic acids can comprise ethyl gallate, ellagic acid, methyl gallate, catechin, gallic acid, and 3,4-dihydroxy benzoic acid. The phenolic acids can be selected from the group consisting of ethyl gallate, ellagic acid, methyl gallate, catechin, gallic acid, and 3,4-dihydroxy benzoic acid.

The composition can comprise about 0.3 w/w % ethyl gallate, about 1.9 w/w % ellagic acid, about 0.02 w/w % methyl gallate, about 0.1 w/w % catechin, about 1.4 w/w % gallic acid, about 0.1 w/w % 3,4-dihydroxy benzoic acid, or combinations thereof. The composition can comprise about 0.3 w/w % ethyl gallate, about 1.9 w/w % ellagic acid, about 0.02 w/w % methyl gallate, about 0.1 w/w % catechin, about 1.4 w/w % gallic acid, and about 0.1 w/w % 3,4-dihydroxy benzoic acid.

The composition can comprise 0.28±0.04 w/w % ethyl gallate, 1.85±0.33 w/w % ellagic acid, 0.02±0.003 w/w % methyl gallate, 0.11±0.008 w/w % catechin, 1.41±0.04 w/w % gallic acid, 0.09±0.01 w/w % 3,4-dihydroxy benzoic acid, or combinations thereof. The composition can comprise 0.28±0.04 w/w % ethyl gallate, 1.85±0.33 w/w % ellagic acid, 0.02±0.003 w/w % methyl gallate, 0.11±0.008 w/w % catechin, 1.41±0.04 w/w % gallic acid, 0.09±0.01 w/w % 3,4-dihydroxy benzoic acid. The composition can comprise about 0.30 w/w % ethyl gallate, about 1.90 w/w % ellagic acid, about 0.02 w/w % methyl gallate, about 0.10 w/w % catechin, about 1.40 w/w % gallic acid, about 0.10 w/w % 3,4-dihydroxy benzoic acid, or combinations thereof.

The composition can comprise chlorogenic acids. The chlorogenic acids can comprise 3-O-caffeoylquinic acid (3-CQA), 5-O-caffeoylquinic acid (5-CQA), 4-O-caffeoylquinic acid (4-CQA), 3,4 di-O-caffeoylquinic acid (3,4-diCQA), 3,5 di-O-caffeoylquinic acid (3,5-diCQA), 4,5 di-O-caffeoylquinic acid (4,5-diCQA), or combinations thereof. The composition can comprise 3-O-caffeoylquinic acid (3-CQA), 5-O-caffeoylquinic acid (5-CQA), 4-O-caffeoylquinic acid (4-CQA), 3,4 di-O-caffeoylquinic acid (3,4-diCQA), 3,5 di-O-caffeoylquinic acid (3,5-diCQA), and 4,5 di-O-caffeoylquinic acid (4,5-diCQA). The chlorogenic acids can be selected from the group consisting of 3-O-caffeoylquinic acid (3-CQA), 5-O-caffeoylquinic acid (5-CQA), 4-O-caffeoylquinic acid (4-CQA), 3,4 di-O-caffeoylquinic acid (3,4-diCQA), 3,5 di-O-caffeoylquinic acid (3,5-diCQA), and 4,5 di-O-caffeoylquinic acid (4,5-diCQA).

The composition can comprise about 0.0005 w/w % 3-CQA, about 0.01 w/w % 5-CQA, about 0.01 w/w % 4-CQA, about 0.02 w/w % 3,4-diCQA, about 0.4 w/w % 3,5-diCQA, about 0.08 w/w % 4,5-diCQA, or combinations thereof. The composition can comprise 0.0005 w/w % 3-CQA, about 0.01 w/w % 5-CQA, about 0.01 w/w % 4-CQA, about 0.02 w/w % 3,4-diCQA, about 0.4 w/w % 3,5-diCQA, and about 0.08 w/w % 4,5-diCQA. The composition can comprise chlorogenic acids selected from the group consisting of 0.0005 w/w % 3-CQA, about 0.01 w/w % 5-CQA, about 0.01 w/w % 4-CQA, about 0.02 w/w % 3,4-diCQA, about 0.4 w/w % 3,5-diCQA, and about 0.08 w/w % 4,5-diCQA.

The composition can comprise 0.00046±0.0001 w/w % 3-CQA, 0.0114±0.006 w/w % 5-CQA, 0.0104±0.004 w/w % 4-CQA, 0.022±0.008 w/w % 3,4-diCQA, 0.388±0.14 w/w % 3,5-diCQA, 0.0823±0.01 w/w % 4,5-diCQA, or combinations thereof. The composition can comprise 0.00046±0.0001 w/w % 3-CQA, 0.0114±0.006 w/w % 5-CQA, 0.0104±0.004 w/w % 4-CQA, 0.022±0.008 w/w % 3,4-diCQA, 0.388±0.14 w/w % 3,5-diCQA, and 0.0823±0.01 w/w % 4,5-diCQA. The composition can comprise chlorogenic acids selected from the group consisting of 00.00046±0.0001 w/w % 3-CQA, 0.0114±0.006 w/w % 5-CQA, 0.0104±0.004 w/w % 4-CQA, 0.022±0.008 w/w % 3,4-diCQA, 0.388±0.14 w/w % 3,5-diCQA, 0.0823±0.01 w/w % 4,5-diCQA, and combinations thereof.

The composition of the invention can be obtained from rose petals. In some aspects, the composition comprises rose petal extract. In other aspects, the composition can be obtained by combining the components disclosed herein (e.g. one or more polyphenols, flavonoids, anthocyanins, phenolic acids, chlorogenic acids, or combinations thereof), wherein the components have been isolated from rose petal extract. The composition can be obtained from red rose petals, yellow rose petals, white rose petals, pink rose petals, blue rose petals, hybrid rose petals, or combinations thereof. The rose petals can be obtained from *R. multiflora, R. chinensis, R. wichuriana, R. canina, R. gallica, R. phoenica, R. damascene, R. alba*, hybrid tea rose, floribundas, Chinese tea rose, hybrid perpetual rose, autumn Damask rose, China rose, or combinations thereof. In embodiments where the composition comprises an extract, it will be understood that all references to weight-to-weight percentages (w/w %) herein shall refer to the percentage weight that the referenced component contributes to the total weight of the extract, absent any other agent or material with which the composition may be in contact with, such as vitamins, pharmaceutical carriers, excipients, binding and bulking agents, etc.

Extracts for use with the invention can be obtained from solvent extraction. The solvent can be an aqueous solvent, alcohol-based solvent, supercritical fluid, or combinations thereof. Non-limiting examples of alcohol-based solvents for use with the invention include, but are not limited to, ethanol, methanol or a combination thereof. The supercritical fluid extraction solvent can be, but is not necessarily limited to, carbon dioxide.

In one non-limiting embodiment, the invention comprises a composition comprising a rose petal extract that comprises 66.44±3.09 w/w % total polyphenols, 9.47±1.23 w/w % total flavonoids, and 2.73±0.38 w/w % total anthocyanins. The flavonoids can comprise 3.48±0.11 w/w % isoquercetin, 0.33±0.02 w/w % rutin, 0.25±0.28 w/w % quercetin, and 0.001±0.00 w/w % taxifolin. The flavonoids can further comprise kaempferol pentoside, quercetin 3-O-xyloside, quercetin 3-O-glucoside, aglycone quercetin, quercetin 3-O-galactoside, kaempferol deoxyhexoside, quercetin 3-O-rhamnoside, kaempferol acetyldisaccharide, and kaempferol 3-0-rutinoside. The composition can comprise phenolic acids, wherein the phenolic acids comprise 0.28±0.04 w/w % ethyl gallate, 1.85±0.33 w/w % ellagic acid, 0.02±0.003 w/w % methyl gallate, 0.11±0.008 w/w %, catechin, 1.41±0.04 w/w % gallic acid, and 0.09±0.01 w/w %3,4-dihydroxy benzoic acid. The composition can comprise chlorogenic acids, wherein the chlorogenic acids comprise 0.00046±0.0001 w/w % 3-O-caffeoylquinic acid (3-CQA), 0.0114±0.006 w/w % 5-O-caffeoylquinic acid (5-CQA), 0.0104±0.004 w/w % 4-O-caffeoylquinic acid (4-CQA), 0.022±0.008 w/w % 3,4 di-O-caffeoylquinic acid (3,4-diCQA), 0.388±0.14 w/w % 3,5 di-O-caffeoylquinic acid (3,5-diCQA), and 0.0823±0.01 w/w % 4,5 di-0-caffeoylquinic acid (4,5-diCQA). The composition can comprise the anthocyanins cyanidin 3-O-glucoside, cyanidin 3-O-rutinoside, delphinidin 3-O-galactoside, and delphinidin 3-O-glucoside.

In a further non-limiting embodiment, the invention comprises a composition comprising a rose petal extract that comprises 66.44±3.09 w/w % total polyphenols, 9.47±1.23 w/w % total flavonoids, and 2.73±0.38 w/w % total anthocyanins. The composition can comprise 3.5 w/w % isoquercetin, 1.8-2.0 w/w % ellagic acid, 1.0-1.5% w/w % gallic acid, 0.3-0.35 w/w % rutin, 0.25 w/w % quercetin, 0.1 w/w % catechins, or combinations thereof. The composition can comprise 3.5 w/w % isoquercetin, 1.8-2.0 w/w % ellagic acid, 1.0-1.5% w/w % gallic acid, 0.3-0.35 w/w % rutin, 0.25 w/w % quercetin, and 0.1 w/w % catechins.

In some aspects of the invention, the composition comprises at least one excipient that is in contact with the mixture. The excipient can be selected on the basis of compatibility with the mixture and the properties of the desired dosage form. Excipients include, but are not limited to, binders, fillers, flow aids/glidents, disintegrants, lubricants, stabilizers, surfactants, and the like. A summary of suitable excipients include, but are not limited to, those disclosed in Remington: The Science and Practice of Pharmacy, 19$^{th}$ Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999) the entire contents of which are incorporated herein by reference for all purposes.

In additional embodiments, the composition may further employ controlled, sustained, or extended release formulations known collectively as "modified release" formulations. The composition can be administered by modified release systems or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Dosage forms for the composition can be used to provide modified release of one or more active ingredients using, for example, hydropropylmethyl cellulose, other polymer matrices, gels, permeable membranes, osmotic systems, multilayer coatings, microparticles, liposomes, microspheres, or a combination thereof. Suitable modified release formulations known to those of ordinary skill in the art, including those described herein, can be readily selected for use with the composition of the invention.

The composition can be in the form of a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, injection, or combinations thereof. The composition can be formulated for oral administration. The composition can be in contact with vitamins, minerals, extracts, amino acids, protein, carbohydrates, lipids, excipients, caffeine, flavorings, sweeteners, preservatives, or combinations thereof.

In some aspects of the invention, the composition is combined with a food, snack, nutritional supplement, dietary supplement, food supplement, or beverage. The food, snack, nutritional supplement, dietary supplement, food supplement, or beverage can have reduced calorie content. For example, the composition can be provided as a means for managing body weight wherein the composition is formulated to provide a dietetic food, a dietetic snack, a dietetic nutritional supplement, a dietetic dietary supplement, a dietetic food supplement, or a dietetic beverage. The composition can be combined with dietetic snacks such as bars, chips, chews, gels, candies, chocolates, cakes, cookies and other pastries, wafers, crackers, ice cream, and the like.

The composition can be provided in bulk quantities for the industrial manufacture of the products and dosage forms described herein. For example, the composition can be provided in bulk quantities as a powder or liquid. Bulk quantities of the composition can be packaged, stored and/or distributed in drums, bags, boxes, and other containers which are configured to prevent or inhibit the oxidation of one or more active components of the composition.

In some aspects, the invention provides a method of making the composition described herein. The method can be practiced by providing, in isolated form, one or more of the polyphenols, flavonoids, anthocyanins, chlorogenic acids, and/or phenolic acids disclosed herein, and combining these components to achieve the composition disclosed herein. In other aspects, the composition can be obtained from one or more rose petal extracts. The composition can be obtained from red rose petals, yellow rose petals, white rose petals, pink rose petals, blue rose petals, hybrid rose petals, or combinations thereof. The rose petals can be rose petals from *R. multiflora*, *R. chinensis*, *R. wichuriana*, *R. canina*, *R. gallica*, *R. phoenica*, *R. damascene*, *R. alba*, hybrid tea rose, floribundas, Chinese tea rose, hybrid perpetual rose, autumn Damask rose, China rose, or combinations thereof. The rose petal extract can be obtained by solvent extraction, extrusion or a combination thereof. The solvent can be an aqueous solvent, alcohol-based solvent, supercritical fluid extraction, or combinations thereof. The extract can be obtained using any suitable alcohol-based solvent capable of providing the composition disclosed herein. Suitable alcohol-based solvents include, but are not limited to, ethanol, methanol, or a combination thereof. The extract can be obtained by any supercritical fluid extraction solvent suitable for obtaining the composition disclosed herein. In one non-limiting embodiment, the supercritical fluid extraction solvent comprises carbon dioxide.

In some aspects, the invention provides a method of treating a metabolic disorder. The method can be practiced by administering the composition disclosed herein to a patient in need thereof. The composition can be administered in an effective amount. The patient can have a metabolic disorder, be suspected of having a metabolic disorder, or at risk of developing a metabolic disorder. Accordingly, administering the composition can prevent the development of the metabolic disorder, inhibit the progression of the metabolic disorder, prevent the development of one or more symptoms of the metabolic disorder, inhibit the progression one or more symptoms of the metabolic disorder, or combinations thereof.

Metabolic disorders treatable by the method of the invention include, but are not limited to, being overweight, obesity, prediabetes, polycystic ovary syndrome, dyslipidemia or disorders of lipid metabolism (e.g. hyperlipidemia), as well as hyperglycemic conditions, such as insulin-dependent (type 1) or -independent (type 2) diabetes, as well as physiological conditions or disorders associated with or that result from the hyperglycemic condition. Thus, hyperglycemic conditions treatable by a method of the invention also include a histopathological change associated with chronic or acute hyperglycemia (e.g., diabetes). Particular non-limiting examples include degeneration of pancreas (beta cell destruction), kidney tubule calcification, degeneration of liver, eye damage (diabetic retinopathy), diabetic foot, ulcerations in mucosa such as mouth and gums, excess bleeding, delayed blood coagulation or wound healing and increased risk of coronary heart disease, stroke, peripheral vascular disease, dyslipidemia, hypertension, obesity.

In some aspects of the invention, administering the composition treats diabetes. Administering the composition can treat a complication associated with diabetes including, but not limited to, retinopathy (i.e., blindness); neuropathy (i.e., nerve damage) which leads to foot ulcers, gangrene, and amputations; kidney damage, which leads to dialysis; and cardiovascular disease. Administering the composition to a patient with diabetes or prediabetes can reduce total blood glucose content, reduce blood insulin, reduce the blood insulin to blood glucose ratio, increase insulin sensitivity, or a combination thereof.

A patient treated for diabetes with the composition can be ineligible for treatment with metformin. The patient can be ineligible for treatment with metformin due to a risk of developing lactic acidosis due to kidney disorders (e.g. renal disease, renal impairment or renal dysfunction), dehydration, unstable or acute congestive heart failure, acute or chronic metabolic acidosis, hereditary galactose intolerance, lung disease, liver disease or heart failure (e.g. unstable or acute congestive heart failure). The patient for diabetes can be an elderly patient ineligible for metformin therapy due to reduced renal function. The patient treated for diabetes can be ineligible for metformin therapy due to one or more metformin side effects including diarrhea, nausea, vomiting, dizziness, headaches and dyspepsia.

Administering the composition to a patient with a metabolic disorder can produce one or more therapeutic effects in the patient. The composition can reduce blood glucose, increase insulin sensitivity, reduce body weight, reduce percent body fat, prevent or inhibit an increase in body fat, increase percent lean mass, reduce serum cholesterol, decrease low density lipoprotein, decrease serum triglycerides, increase high density lipoprotein, or combinations thereof. In some aspects of the invention, administering the composition to the patient alters glucose metabolism in the patient. Such alteration can include any measurable change in at least one aspect of glucose metabolism including, but not limited to, total blood glucose content, blood insulin, the blood insulin to blood glucose ratio, insulin sensitivity, or oxygen consumption.

In some aspects of the invention, the invention provides a method of treating dyslipidemia (e.g. hyperlipidemia). In such methods, the patient can have elevated blood levels of total lipid content, HDL cholesterol, LDL cholesterol, VLDL cholesterol, triglyceride, Lp(a), apo A-I, apo E, non-esterified fatty acids, or combinations thereof. Administering the composition to such patients can reduce one or more of these levels, as well as improve the ratio of HDL to LDL in such patients.

In some aspects, the invention provides a method of treating obesity in a patient in need thereof. The patient can be, or at risk of being, overweight or obese. Accordingly, administering the composition to the patient can reduce body weight, reduce percent body fat, increase percent lean mass, prevent weight gain, or combinations thereof. Administering the composition can treat a complication associated with obesity or being overweight. Such complications include, but are not limited to, hypercholesterolemia, hypertension, dyslipidemia (for example, high total cholesterol or high levels of triglycerides), type 2 diabetes, coronary heart disease, stroke, gallbladder disease, osteoarthritis, sleep apnea and respiratory problems, and some cancers (endometrial, breast, and colon).

In some aspects, the invention provides a method for health maintenance and supplementing the dietary and nutritional intake of a patient. Such methods can be practiced by administering to a patient in need thereof the composition as disclosed herein. Administering the composition can improve the health of the patient, improve the dietary and nutritional intake of the subject, or a combination thereof.

Administering the composition can improve the health of the patient by increasing antioxidant activity in the subject. The composition can be combined with one or more foods, beverages, dietary and nutritional supplements, or combinations thereof, and administered to the patient.

One aspect of the invention concerns the dosage of the composition. The composition can be administered at a dose of between about 5 mg/day to about 500 mg/day. The composition may be administered at a dose between about 20 mg/day to about 1 mg/day. The composition of the invention may be administered at a dose of about 20 mg/day, about 21 mg/day, about 22 mg/day, about 23 mg/day, about 24 mg/day, about 25 mg/day, about 26 mg/day, about 27 mg/day, about 27 mg/day, about 28 mg/day, about 29 mg/day, about 30 mg/day, about 31 mg/day, about 32 mg/day, about 33 mg/day, about 34 mg/day, about 35 mg/day, about 40 mg/day, about 45 mg/day, about 50 mg/day, about 100 mg/day, about 150 mg/day, about 200 mg/day, about 250 mg/day, about 300 mg/day, about 350 mg/day, about 400 mg/day, about 450 mg/day, or about 500 mg/day, as well as any dosage intervening these specifically disclosed amounts. The composition can be administered at a dosage of between about 400 mg/day to about 500 mg/day, between about 300 mg/day to about 400 mg/day, between about 200 mg/day to about 300 mg/day, between about 100 mg/day to about 200 mg/day, between about 100 mg/day to about 200 mg/day, or about 20 mg/day to about 100 mg/day. It is contemplated that the composition can be administered at any dosage that intervenes the dosages called out in this specification. The composition may be administered to the patient topically, orally, buccally, sub-lingually, parenterally, intravenously, intranasally, intravaginally, rectally, inhalation, or combinations thereof.

The present disclosure is further described in the light of the following non-limiting examples which are set forth for illustration purposes only and not to be construed for limiting the scope of the disclosure.

EXAMPLES

Example 1 illustrates a method of making an embodiment of the inventive composition. Example 2 describes the phytochemical analysis and content of the composition from Example 1. Example 3 describes the virtual screening of active components of the composition from Example 1 for interaction with key proteins involved in metabolic disorders such as obesity and type 2 diabetes. Example 4 relates to the determination of antioxidant potentials of the composition from Example 1. Example 5 describes anti-lipase and α-glucosidase inhibition studies using the composition from Example 1. Example 6 relates to the use of the composition from Example 1 in the regulation of adipocyte differentiation using 3T3L-1 preadipocytes. Example 7 shows DPPH scavenging activity, superoxide anion scavenging activity, and the reducing power of the composition from Example 1.

The composite bioactive fraction from petals of different rose varieties were obtained and analyzed for the presence of phytochemicals. The bioactive fraction was further examined for anti-obesity and antidiabetic effects using in silico and in vitro experimental approaches. Extraction process yielded not less than 12% of product. Results of the quantitative spectrophotometric analysis indicated that the composition contained not less than 66 w/w % of the total polyphenols comprising 9.5 w/w % flavonoids and 2.7 w/w % anthocyanins. Further quantitative determination through LCMS/MS and HPLC indicated major bioactive compounds such as quercetin, isoquercetin, ellagic acid, rutin, ethyl gallate, catechin, and isomers of chlorogenic acid. Qualitative fingerprint analysis revealed the presence of quercetin, isoquercetin, rutin, kaempferol and their derivatives, and anthocyanins. Results of virtual screening revealed that active principles in the composition such as isoquercetin and kampferol 3 rutinoside showed strong binding affinity to PPARα and γ ligand binding sites. These results indicated the agonists in the composition target metabolic diseases. Further, analysis revealed the composition as an antioxidant and an inhibitor of the metabolic enzymes pancreatic lipase (IC50=81.4 µg/mL) and α-glucosidase (IC50=1.33 µg/mL). The anti-adipogenic activity of the composition was evident from its lipid lowering effects in 3T3-L1 adipocytes. Western blot analysis showed that the composition regulated adipogenesis by downregulating the expression of PPARγ and C/EBPα proteins in adipocytes.

Example 1—Preparation of an Embodiment of the Composition

The extraction processes described in the present invention can be scaled up to produce larger quantities of the inventive composition. The details provided for preparation of the composition of the present invention reflect the presently preferred method and should not be considered as limiting. The quantities and times described below can be varied substantially to provide suitable extract from petals of Rosa multiflora and other red rose varieties in accordance with the invention.

50 kg of shade dried rose petals were taken into a clean vertical 1.0 KL extractor. The bottom of the extractor comprised of a perforated plate on which filtration cloth was fixed. The bottom of the extractor was connected to a transfer pump, input and outputs of the transfer pump connected to T bend. One end was connected to extractor top for circulation of extraction mass while extraction and other end of T bend was connected to receiver tank.

The above mentioned mass was extracted with 7-8 bed volumes of 50 v/v % of ethanol. Extraction was continued at 75-80° C. temperature about 7-8 hrs with continuous circulation of extract with transfer pump. After completion of extraction, the extract was filtered through a 5 micron SS candle filter and clear extract was collected in a receiver tank. The bed was re-extracted by adding 5-6 bed volumes of 50 v/v % ethanol three more times at 75-80° C. for about 7-8 hrs and filtered through a 5 micron SS candle filter. All the extracts were collected in a receiver tank and the combined extract was concentrated in a reactor under vacuum at 75-80° C. to evaporate the solvent and until the extract was free from ethanol and TDS reaches to 50-70 w/v %. The reactor was cooled to room temperature. Concentrated extract was dried in a vacuum tray drier at 70-75° C. under vacuum till dryness. Weight of the dried extract was about 18.5±1.5 kg.

120-150 litres of 95-96 v/v % of ethanol was charged into a clean dry 0.5 kl reactor. The above dried extract was added into the reactor under stirring about 15-20 minutes at room temperature. Stirring was continued about one hour at room temperature and then filtered. The collected filtrate was dried under vacuum.

The above filtrate was taken into a clean dry 0.5 kl reactor and concentrated under vacuum at 75-80° C. till the volume reached to 10-15 litres. Concentrated liquid was dried in a vacuum tray drier at 70-75° C. under vacuum to dryness. Weight of the dried product was about 6±0.5 kg. The final dried product was milled in suitable multimill and passed through 60 mesh sieve. The resulting composition was tested for quantitative and qualitative determination of phytoconstituents and biological effects in accordance with the following examples.

Example 2—Phytochemical Analysis

Estimation of total polyphenols by Folin-Ciocalteu's method (Singleton et al. 1999)
Preparation of Standard Curve:

Weighed appropriate amount of gallic acid (99% pure) was taken in a 100 mL volumetric flask; dissolved by adding 50% methanol solution (0.25 mg/mL) and then further diluted to 20, 40, 60, 80, 100 and 120 µg/mL. One mL aliquot of each dilution was taken in a test tube and mixed with 15 mL of 50% methanol solution. Then 1.0 mL Folin Ciocalteu's reagent was added and allowed to incubate at room temperature for 10 minutes. 3.0 mL of 20% (w/w) $Na_2CO_3$ was added in each test tube, followed by incubation at 40° C. in a water bath for 30 min and allowed to cool at room temperature. Absorbance of the standard was measured at 755 nm using UV/VIS spectrophotometer (Schimadzu, Japan) against blank, i.e., 50% methanol.
Sample Preparation 25 mg of the inventive composition was taken into 100 mL volumetric flask; dissolved by adding 65-70 mL of 50% methanol solution and the volume made up to the mark with 50% methanol.
Procedure 15 mL of 50% methanol solution was taken into a test tube. To this 1.0 mL of Folin-Ciocalteu reagent was added followed by 1 mL of sample solution. The reaction mixture was allowed to incubate at room temperature for 10 minutes. 3.0 mL of 20% (w/w) $Na_2CO_3$ was added in each test tube, followed by incubation at 40° C. in a water bath for 30 min and allowed to cool at room temperature. The absorbance of the reaction mixture was measured at 755 nm using UV/VIS spectrophotometer (Schimadzu, Japan) against blank, i.e., 50% methanol. The percentage of total polyphenols was determined as below:

$$\% \text{ Total polyphenols} = \frac{\frac{A_{sample} - C}{m} \times DF \times 100}{W_{sample} \times 1000}$$

Where, $W_{sample}$— Sample weight in grams, DF—Dilution factor, $A_{sample}$—Sample absorbance, C— Intercept obtained from calibration graph and m—Slope from calibration graph.

Estimation of total flavonoids content (Chang et al. 2002)
Preparation of Standard Curve Weighed appropriate amount of Quercetin (99% pure) was dissolved in 100 mL of 80% methanol solution (0.25 mg/mL) and then further diluted to 20, 40, 60, 80, 100 and 120 µg/mL. 2.0 mL aliquot of each dilution was taken in a test tube and mixed with 6 mL of methanol. Then 0.4 ml of 1M potassium acetate and 11.2 ml of distilled water were added to the reaction mixture. A volume of 10% aluminum chloride was substituted by the same volume of distilled water in the blank and allowed to incubate at room temperature for 30 minutes. Absorbance of the standard (reaction mixture) was measured at 415 nm using UV/VIS spectrophotometer (Schimadzu, Japan) against blank, i.e., 80% methanol.

Sample Preparation 25 mg of the inventive composition was taken into 50 mL of volumetric flask. Dissolved by adding 25-30 mL of 80% methanol and the volume was made up to the mark with diluent.

Procedure

The reaction mixture was prepared by adding 6 mL of methanol, 0.4 mL of potassium acetate, 11.2 mL of distilled water and 2 mL of sample solution. The reaction mixture was allowed to incubate at room temperature for 30 minutes. The absorbance of the reaction mixture was measured at 415 nm using UV/VIS spectrophotometer (Schimadzu, Japan) against blank (80% methanol). The percentage of total flavonoids was determined as below:

$$\% \text{ Total polyphenols} = \frac{\frac{A_{sample} - C}{m} \times DF \times 100}{W_{sample} \times 1000}$$

Where, $W_{sample}$—Sample weight in grams, DF—Dilution factor, $A_{sample}$—Sample absorbance, C—Intercept obtained from calibration graph and m—Slope from calibration graph.

Estimation of total anthocyanins content (Giusti et al. 1999)

Sample Preparation 20 mg of the composition was taken into 50 mL of volumetric flask; dissolved by adding 25-30 mL of 2% HCl—methanol solution, the volume was made up to the mark with 2% HCl—methanol solution.

Procedure

The absorbance of the reaction mixture was recorded at 535 nm using UV/VIS spectrophotometer (Schimadzu, Japan) against blank, i.e., 2% HCl—methanol solution. The percentage of total anthocyanins was determined as below:

$$\% \text{ Total polyphenols} = \frac{A_{sample} \times DF \times 100}{72 \times W_{sample}}$$

Where, $A_{sample}$—Sample absorbance, DF—Dilution factor, $W_{sample}$—Sample weight in grams and 72-Absorptivity (absorbance of 1 mg/ml) of malvidin-3-glucoside at 535 nm.

The results of quantitative phytochemical analysis are tabulated in Table 1. The data were expressed as mean±SEM of three independent experiments.

TABLE 1

Quantitative analysis by spectrophotometric method

| Analysis | Quantity (w/w %) |
| --- | --- |
| Total polyphenols | 66.44 ± 3.09 |
| Total flavonoids | 9.47 ± 1.23 |
| Total anthocyanins | 2.73 ± 0.38 |

Quantitative Determination of Phytochemicals

Quantitative Analysis of Flavonoid Composition by Liquid Chromatography-Mass Spectrometry (LCMS) Analysis Mass Parameters MS detection: ESI −ve Mode
DL temperature: 250° C.
Heat block Temperature: 400° C.
Interface Temperature: 300° C.
Nebulizing Gas flow: 3 L/min
Drying Gas flow: 15 L/min
Heating Gas flow: 5 L/min Analytical Parameters System: LCMS/MS 8050
Column: XB-C18, 2.6 µm, 150×2.1 mm Phenomenex (Kinetex).
Flow rate: 0.3 mL/min
Volume of injection: 2 µL
Run time: 15 min
Mobile phase: A: 1% Glacial acetic acid
  B: 1% Glacial acetic acid:Acetonitrile (50:50)
Gradient:

| Time | B % Concentration |
| --- | --- |
| 0.01 | 45 |
| 10.0 | 100 |
| 11.5 | 100 |
| 12.5 | 45 |
| 15.0 | Stop |

Materials

Rutin (94%), isoquercetin (90%), taxifolin (85%), naringenin (95%) and isoquercetin (90%) reference standards were obtained from Sigma-Aldrich (India) and quercetin (99%) reference standard was obtained from SD Fine Chemicals Ltd.

Preparation of Standard Solution

Accurately weighed appropriate amounts of rutin (94%), quercetin (98%), isoquercetin (90%), taxifolin (85%) and naringenin (95%) reference standards were dissolved in methanol:DMSO (9:1) in a 25 ml volumetric flask to obtain a stock solution of 48, 40, 40, 44 and 44 ppm respectively. Working standard solutions were obtained by diluting the standard stock solution to 50 ml volumetric flask and made up with methanol to get a final concentration of 100 ppb individual.

Sample Preparation

Weighed 25 mg of dried sample was taken in 50 ml of volumetric flask and dissolved in methanol:DMSO (9:1). Pippeted 1.0 ml of sample solution and made up to the mark by using diluent methanol. Filtered the sample solutions through 0.2 micron nylon syringe filter and injected the solution.

Calculation:

$$\text{Assay \%} = \frac{\text{Peak area of the sample} \times \text{Conc. of the } STD \times \text{purity of the } STD}{\text{Peak area of the standard} \times \text{Conc. of the sample}}$$

Determination of Phenolic Acids by LCMS Analysis

Mass Parameters

MS detection: ESI −ve Mode
DL temperature: 300° C.
Nebulizing Gas flow: 3 L/min
Heat block Temperature: 400° C.
Drying Gas: 15 L/min Analytical Parameters System: LCMS/MS 8040
Column: C18, 2.6 µm, 150×2.1 mm Phenomenex (Kinetex).
Flow rate: 0.4 mL/min
Volume of injection: 1 µL
Run time: 18 min
Mobile phase A: A: 0.5% Glacial acetic acid B: Methanol
Diluent: Methanol
Gradient:

| Time | B % Concentration |
|---|---|
| 0.01 | 15 |
| 6.0 | 35 |
| 13.7 | 100 |
| 15.0 | 100 |
| 16.5 | 15 |
| 18.0 | Stop |

Materials

Ethyl gallate (98%) and methyl gallate (98%) reference standards were obtained from Himedia. Ellagic acid (95%) reference standard was obtained from Sigma-Aldrich (India). Gallic acid (98%) reference standard was obtained from SRL.3.4-dihydroxy benzoic (97%) reference standard was obtained from Spectrochem. Catechin (98%) reference standard was obtained from Chromadex.

Preparation of Standard Solution

Accurately weighed appropriate amounts of ethyl gallate, ellagic acid, methyl gallate, catechin, gallic acid and 3.4-dihydroxy benzoic acid reference standards were dissolved in methanol to get a final concentration of 80, 180, 132, 132, 120 and 128 ppm respectively.

Preparation of Sample Solution

Weighed 25-30 mg of dried sample in 10 ml of volumetric flask and made up to the mark by using diluent methanol and dissolved. Filtered the sample solutions through a 0.2 micron nylon syringe filter and injected the solution.

Calculation:

$$\text{Assay \%} = \frac{\text{Peak area of the sample} \times \text{Conc. of the } STD \times \text{purity of the } STD}{\text{Peak area of the standard} \times \text{Conc. of the sample}}$$

Determination of Chlorogenic Acids by HPLC Analysis
Column: XBC-18, 5 μm, 150×4.6 mm Phenomenex (Kinetex).
System: LC 2030 C Prominence-i
Flow rate: 1 ml/min
Wavelength: 325 nm
Volume of injection: 5 μl
Run time: 20 min.
Mobile phase: Phase A-0.2% formic acid
    Phase B—Acetonitrile

| Time(min) | Pump B |
|---|---|
| 0.01 | 9 |
| 6.0 | 9 |
| 6.1 | 12 |
| 9.0 | 12 |
| 12.6 | 35 |
| 13.2 | 35 |
| 14.0 | 9 |
| 20.0 | Stop Time |

Materials: 5-O-caffeoylquinic acid (5-CQA) (98%) reference standard was obtained from Sigma Aldrich.

Preparation of Standard Solution

Accurately weighed 10 mg of 5-CQA reference standard was taken in a 50 ml standard volumetric and dissolved in 70% methanol to get a final concentration of 200 ppm.

Preparation of Sample Solution

Weighed 50 mg of dried sample in 50 ml of volumetric flask and make up to the mark by using diluent 70% methanol and dissolved. Filtered the sample solutions through a 0.2 micron nylon syringe filter and injected the solution.

Calculation:

$$\text{Assay \%} = \frac{\text{Peak area of the sample} \times \text{Conc. of the } STD \times \text{purity of the } STD}{\text{Peak area of the standard} \times \text{Conc. of the sample}}$$

Table 2 shows the quantitative analysis of bioactive compounds

| Group | Phytochemical | Method of analysis | Quantity (w/w %) |
|---|---|---|---|
| Flavonoids | Isoquercetin | LCMS/MS | 3.48 ± 0.11 |
| | Rutin | | 0.33 ± 0.02 |
| | Quercetin | | 0.25 ± 0.28 |
| | Taxifolin | | 0.001 ± 0.00 |
| Phenolic acids | Ethyl Gallate | LCMS/MS | 0.28 ± 0.04 |
| | Ellagic Acid | | 1.85 ± 0.33 |
| | Methyl Gallate | | 0.02 ± 0.003 |
| | Catechin | | 0.11 ± 0.008 |
| | Gallic Acid | | 1.41 ± 0.04 |
| | 3,4-Dihydroxy Benzoic Acid | | 0.09 ± 0.01 |
| Chlorogenic acids | 3-O-caffeoylquinic acid (3-CQA) | HPLC | 0.00046 ± 0.0001 |
| | 5-O-Caffeoylquinic acid (5-CQA) | | 0.0114 ± 0.006 |
| | 4-O-Caffeoylquinic acid (4-CQA) | | 0.0104 ± 0.004 |
| | 3,4 Di-O-caffeoylquinic acid (3,4-DiCQA) | | 0.022 ± 0.008 |
| | 3,5 Di-O-caffeoylquinic acid (3,5-DiCQA) | | 0.388 ± 0.14 |
| | 4,5 Di-O-caffeoylquinic acid (4,5-DiCQA) | | 0.0823 ± 0.01 |

Figure 1B:
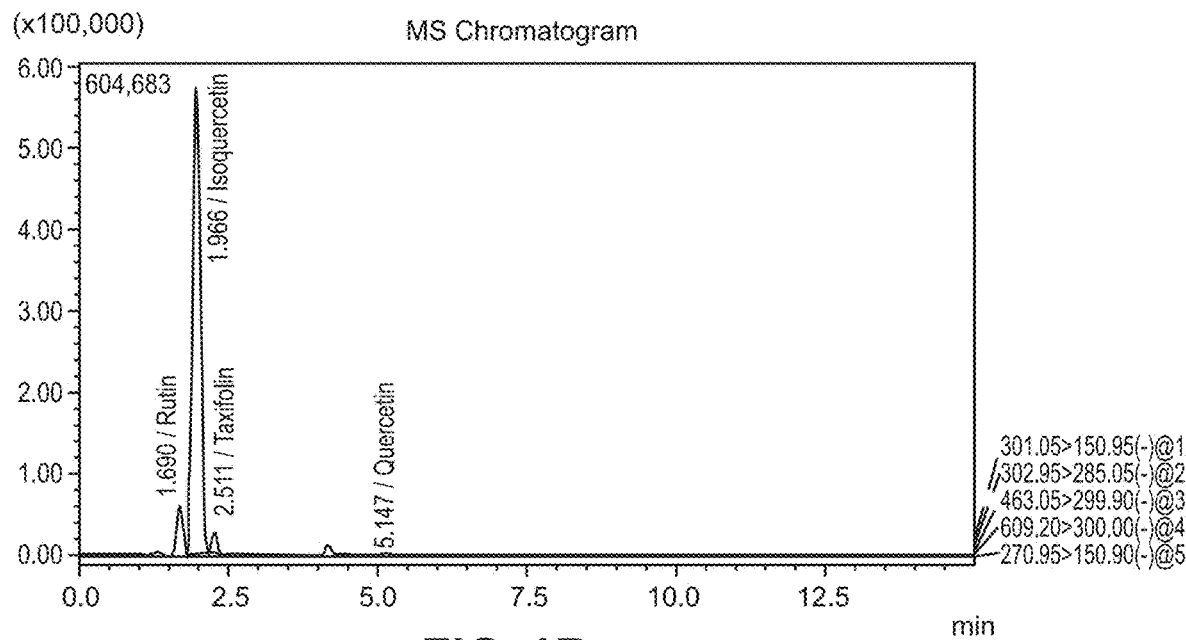
Figure 2A:
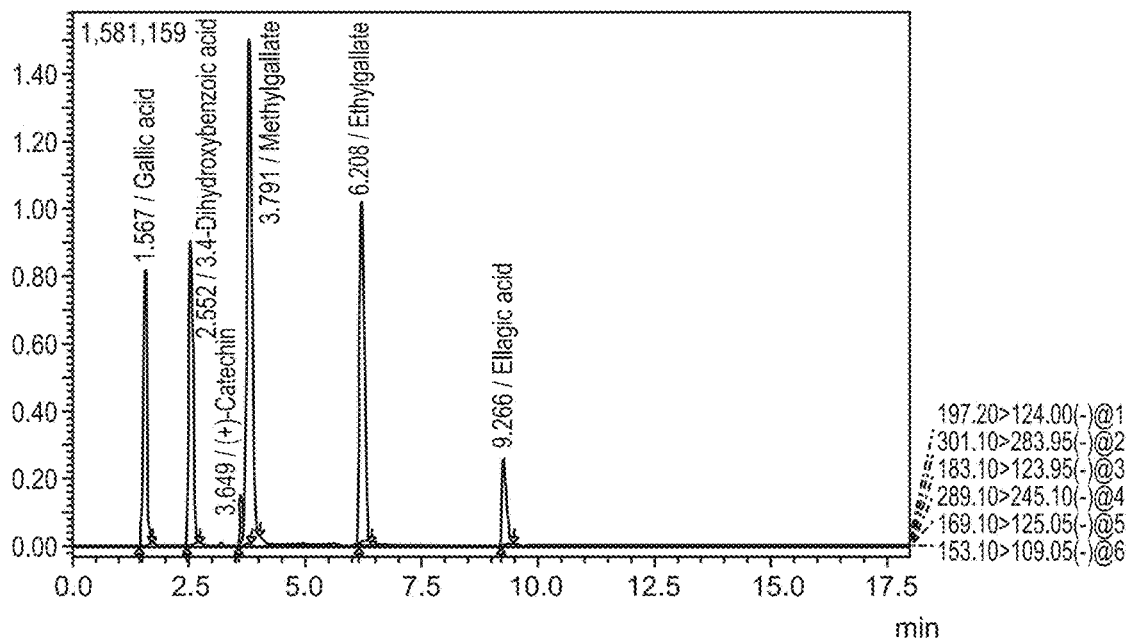
FIGS. 2A and 2B show the LCMS chromatograms of phenolic acids present in an embodiment of the composition.
Figure 2B:
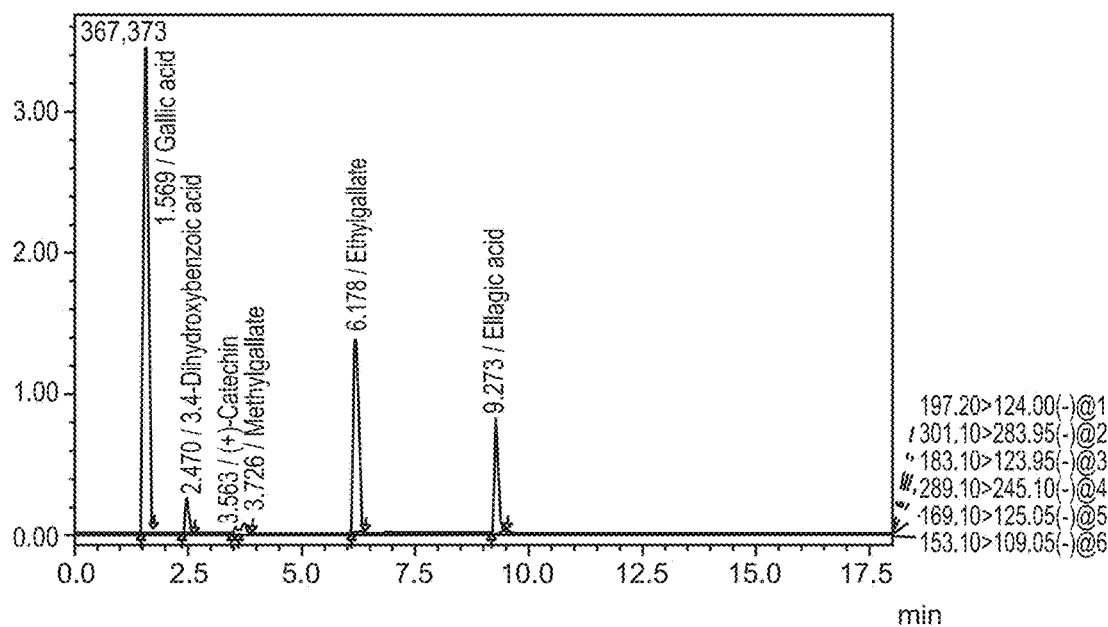
Figure 3A:
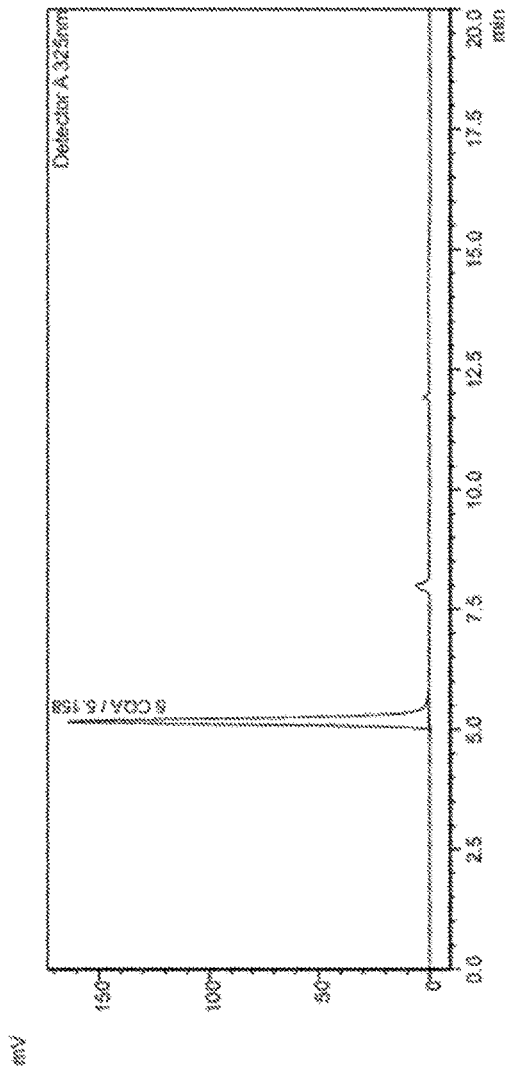
FIGS. 3A and 3B show the HPLC chromatograms of chlorogenic acids present in an embodiment of the composition.
Figure 3B:
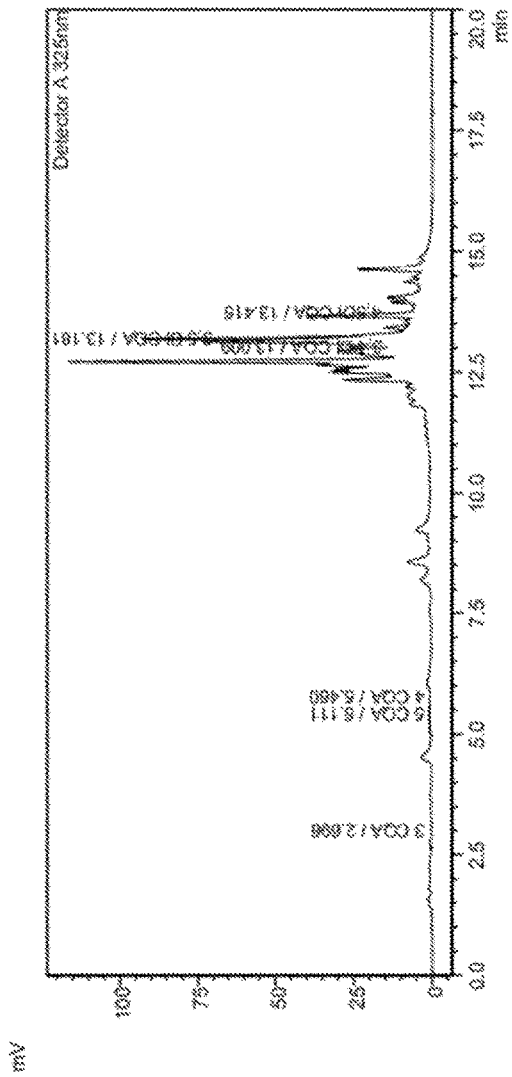

The respective chromatograms for the LCMS analysis of flavonoids, phenolic acids and chlorogenic acids in the inventive composition are shown in FIGS. 1-3.

Qualitative Analysis of Phytoconstituents by Liquid Chromatography-Mass Spectrometry (LCMS) Analysis
Fingerprint Analysis of Anthocyanins
Preparation of Sample Solution Weighed 25 mg of dried sample in 25 ml of volumetric flask and made up to the mark by using diluent (2% hydrochloric acid in methanol) and dissolved. Filtered the sample solutions through a 0.2 micron nylon syringe filter and injected the solution.

Analytical Parameters
System: LCMS/MS 8040
Column: C18, 2.6 μm, 150×2.1 mm Phenomenex (Kinetex)
Flow rate: 0.4 mL/min
Volume of injection: 3 μL
Run time: 35 min
Mobile phase: Phase A-3% formic Acid in water
    : Phase B—Acetonitrile
DL Temp.: 250° C.
Nebulizing gas flow: 3 L/min.
Heat block temp: 400° C.
Drying gas flow: 15 L/min.
MS detection: ESI+ve mode Gradient:

| Time | B concentration |
|---|---|
| 0.01 | 6 |
| 2.90 | 6 |
| 11.60 | 12 |
| 28.90 | 20 |
| 32.00 | 6 |
| 35.00 | Stop |

Fingerprint Analysis of Flavonoids
Preparation of Sample Solution

Weighed 25 mg of dried sample in 25 ml of volumetric flask and made up to the mark by using diluent (70% Methanol) and dissolved. Filtered the sample solutions through 0.2 micron nylon syringe filter and injected the solution.
Analytical Parameters
System: LCMS/MS 8040
Column: C18, 2.6 µm, 150×2.1 mm Phenomenex (Kinetex)
Flow rate: 0.3 mL/min
Volume of injection: 5 µL
Run time: 45 min.
Mobile phase: Phase A—0.5% Acetic Acid in water
 : Phase B—Methanol
DL Temp.: 250° C.
Nebulizing gas flow: 3 L/min.
Heat block temp: 400° C.
Drying gas flow: 15 L/min.
MS detection: ESI+& −ve mode
Gradient:

| Time | B concentration |
|---|---|
| 0.01 | 10 |
| 32.00 | 55 |
| 39.00 | 100 |
| 42.00 | 10 |
| 45.00 | Stop |

Figure 4:
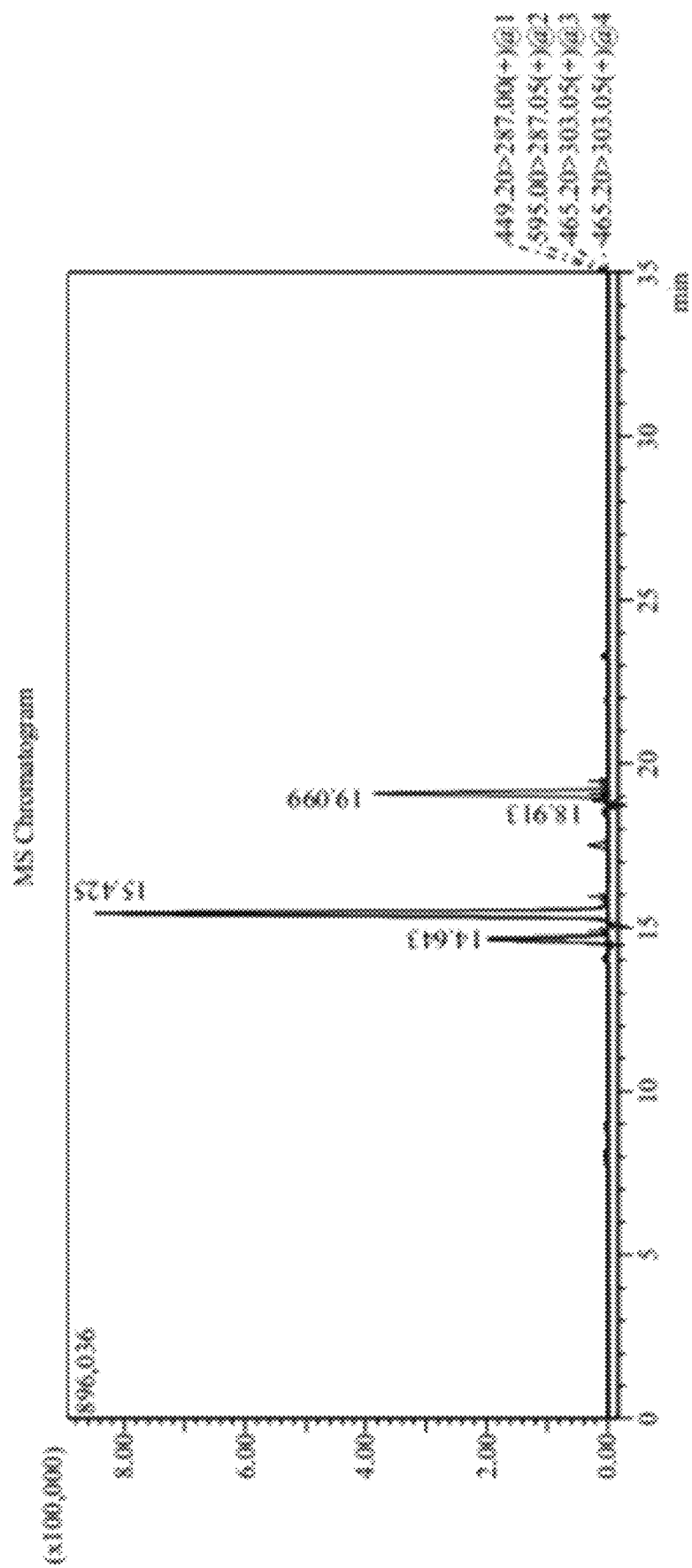
FIG. 4 is an LCMS chromatogram showing the fingerprint analysis of anthocyanins present in an embodiment of the composition.
Figure 5:
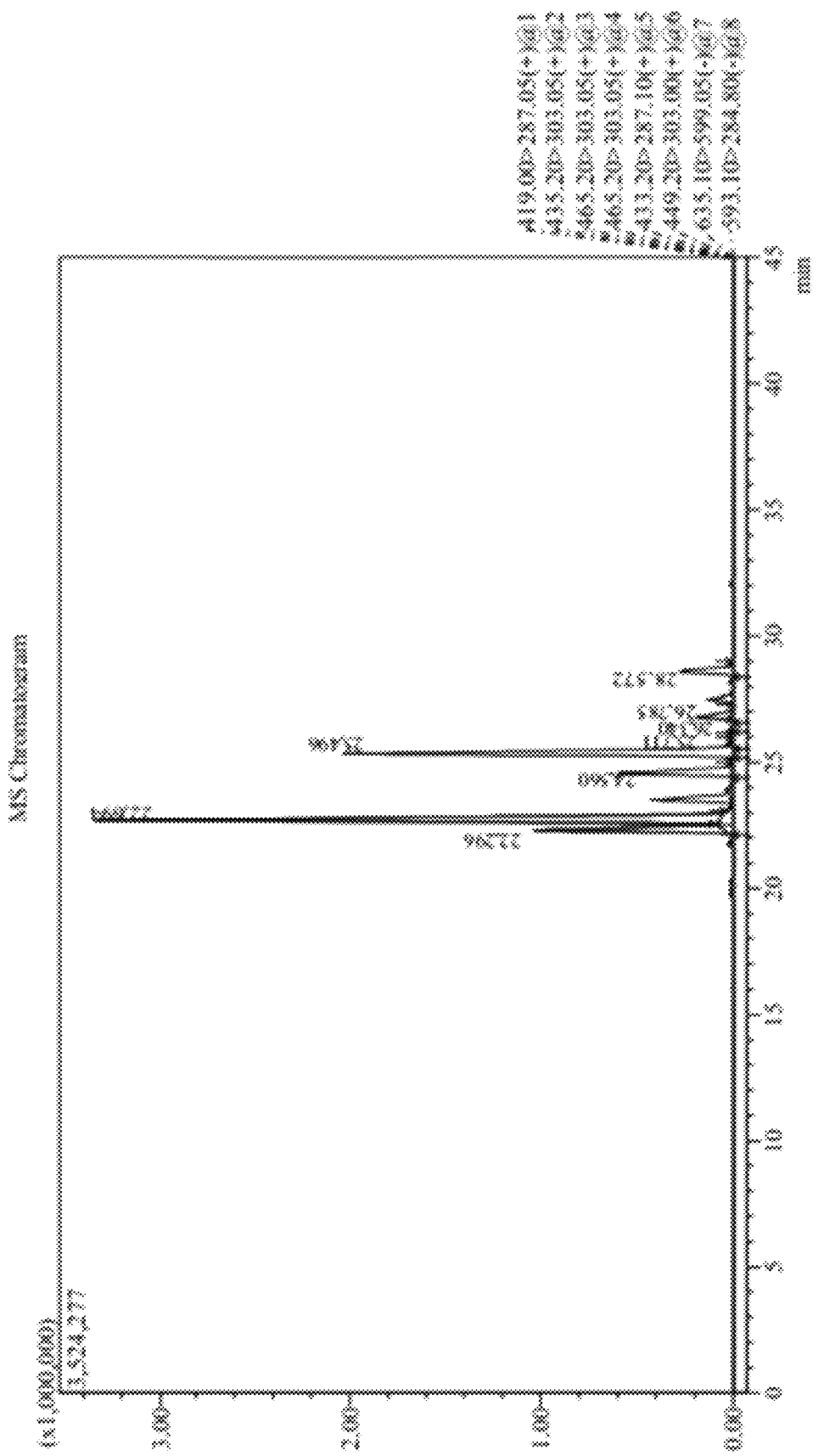
FIG. 5 is an LCMS chromatogram showing the fingerprint analysis of the flavonoids present in an embodiment of the composition.

Table 3 shows the presence of various phytochemicals present in the composition. The spectral details of fingerprint analysis are presented in FIGS. 4 and 5.

| | Bioactive constituent | Retention time | m/z |
|---|---|---|---|
| Anthocyanins | Cyanidin 3-O-Glucoside | 19.099 | 449.20 > 287.00 |
| | Cyanidin 3-O-Rutinoside | 18.913 | 595.00 > 287.05 |
| | Delphinidin 3-O-Galactoside | 14.643 | 465.20 > 303.05 |
| | Delphinidin 3-O-Glucoside | 15.425 | 465.20 > 303.05 |
| Flavonoids | Kaempferol pentoside | 26.785 | 419.00 > 287.05 |
| | Quercetin 3-O-xyloside | 24.560 | 435.20 > 303.05 |
| | Quercetin 3-O-glucoside | 22.694 | 465.20 > 303.05 |
| | Quercetin 3-O-galactoside | 22.296 | 465.20 > 303.05 |
| | Kaempferol deoxyhexoside | 28.572 | 433.20 > 287.10 |
| | Quercetin 3-O-rhamnoside | 25.496 | 449.20 > 303.00 |
| | Kaempferol acetyldisaccharide | 26.340 | 635.10 > 599.05 |
| | Kaempferol 3-O-rutinoside | 25.711 | 593.10 > 284.80 |

Example 3—Structure-Based Virtual Screening and Identification of PPARα/γ Dual Agonists The nuclear receptors called peroxisome proliferator-activated receptors (PPARs) play a vital role in the regulation of metabolic homeostasis. These receptors regulate the genes involved in lipid and glucose metabolism, adipogenesis and energy balance. There are three PPARs known: α, γ and δ. It is reported that PPARα modulates the lipid metabolism and inflammation in tissues with high rate of fatty acid catabolism (Harmon et al. 2011). PPARγ is associated with lipogenesis and fat storage in adipocytes. PPARγ also enhances insulin sensitivity in skeletal muscle (Zieleniak et al. 2008).

To discover PPAR agonists in the inventive composition that target both PPARα and γ, virtual screening was performed using ligand docking tool (Schrödinger).

In the present invention the molecular docking studies of the active agents in the composition with the ligand binding domain (LBD) of PPARα and γ was performed. The crystal structures of PPARα (PDB ID: 2ZNN) and γ (PDB ID: 1ZGY) were retrieved from the RCSB protein data bank (PDB). The protein structures for docking were pre-processed and refined using the following procedures by the Protein Preparation Wizard in the Schrödinger software suite, including adding hydrogen atoms, assigning partial charges and protonation states, and structure minimizing.

The ligand structures were downloaded from Pubchem and saved in SDF file format. Subsequently they were prepared using LigPrep (Schrödinger) by modifying the torsions and assigning protonation states. In Glide (Schrödinger), 32 stereochemical structures were generated per ligand with possible states at target pH 7.0±2.0 using Ionizer, tautomerized, desalted and optimized by producing lowenergy 3D structure for the ligand under the OPLS 2005 force field while retaining the specified chiralities of the input Maestro file.

Receptor grids were calculated for prepared proteins such that various ligand poses bind within the predicted active site during docking. In Glide, grids were generated keeping the default parameters of van der Waals scaling factor 0.8 and charge cutoff 0.25 subjected to OPLS 2005 force field. A cubic box of specific dimensions centered around the centroid of the active site residues (predicted by Sitemap) was generated for each receptor.

Extra precision ligand docking was performed in Glide of Schrödinger-Maestro v11.2. Van der Waals scaling factor and partial charge cutoff was selected to be 0.80 and 0.25, respectively for ligand atoms. Final scoring was performed on energy-minimized poses and displayed as Glide score. The best docked pose with lowest Glide score value was recorded for each ligand.

Docking score of the inventive composition with LBD of PPARα and γ are presented in Table 4 and Table 5 respectively.

Figure 6A:
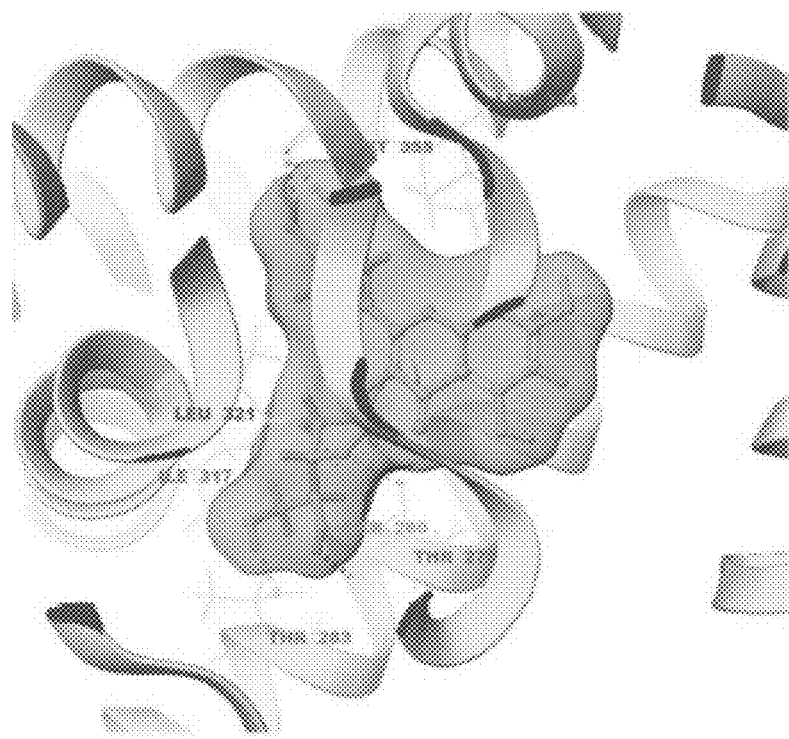
FIGS. 6A and 6B are cartoon representations of isoquercetin (FIG. 6A) and Kaempferol 3-O-rutinoside (FIG. 6BA) in bound conformations with the PPARα ligand binding site.
Figure 6B:
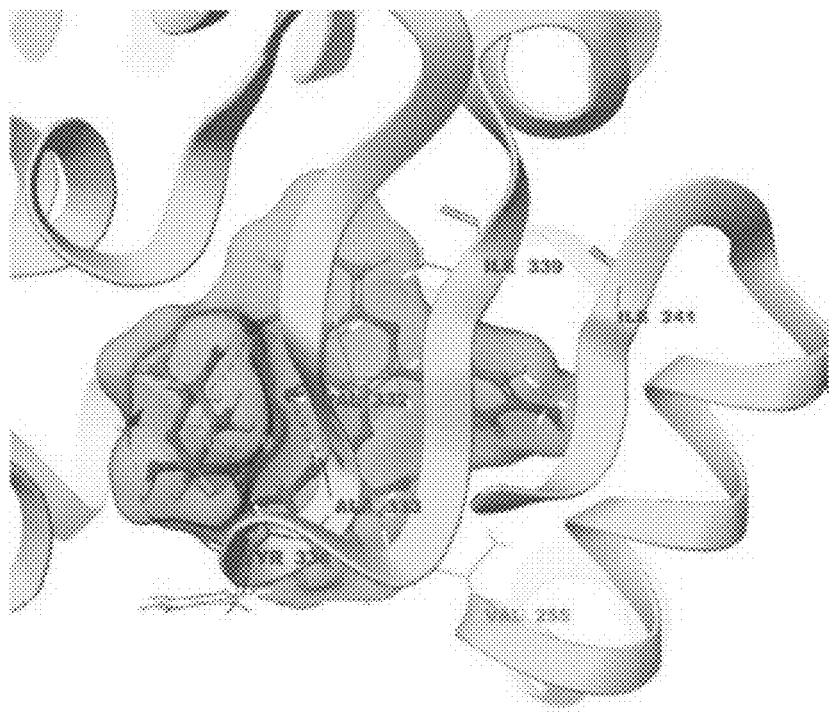
Figure 7A:
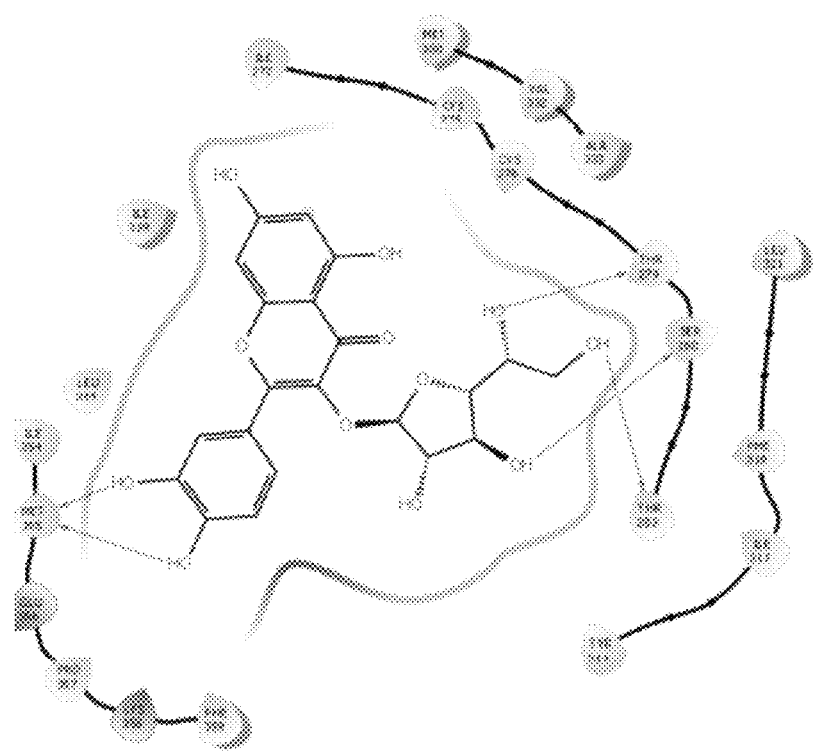
FIGS. 7A and 7B show the interaction of isoquercetin and kaempferol 3-O-rutinoside with the ligand binding domain of PPARα.
Figure 7B:
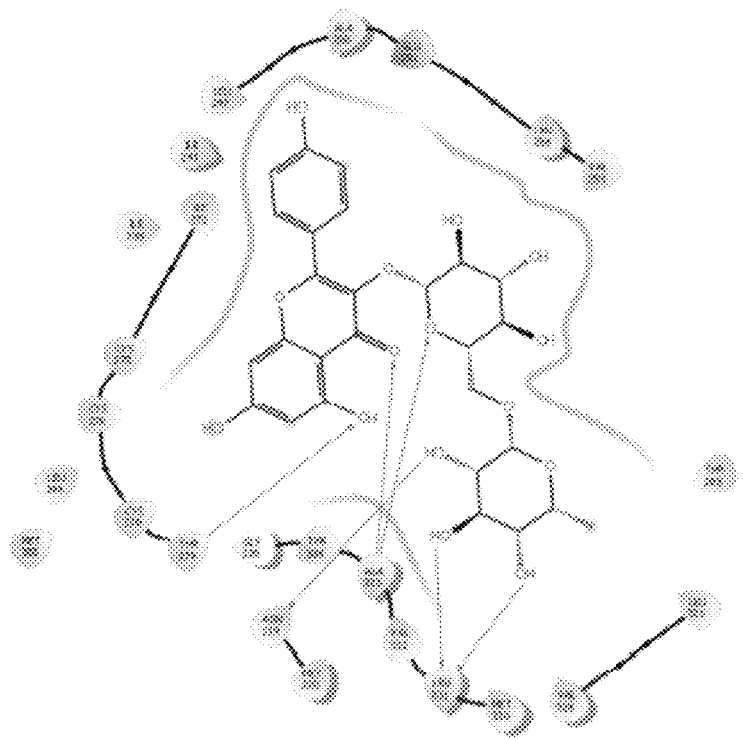

The polyphenols in the inventive composition showed favorable interactions with the LBD of PPARα (FIGS. 6A and 6B). The best fit ligands were found to be isoquercetin and Kaempferol 3-rutinoside with Glide score of −14.0 and −13.0 respectively which is better than the original ligand TIPP703. Isoquercetin had strong H-bonding with amino acid residues Thr279 and Ser280 in addition to Met355 and Thr283 (FIG. 7A). Kaempferol 3-rutinoside interaction with PPARα LBD was similar to that of Fenofibrate (Fibrate drug, PPARα agonist) having interactions with Thr279 and Ala333 (FIG. 7B). These interactions are attributed to the binding of phytochemicals of the composition into the PPARα binding domain.

TABLE 4

Docking score of polyphenols and PPARα ligand binding domain

| Ligands | GScore | LipophilicEvdW | HBond | Interactions |
|---|---|---|---|---|
| Isoquercetin | −14.0 | −5.2 | −6.1 | Thr279, Ser280, Met355, Thr283 |
| Kaempferol 3-rutinosde | −13.0 | −6.6 | −4.7 | Thr279, Tyr334, Ala333 |
| Quercetin 3-galactoside | −12.2 | −5.6 | −4.2 | Ile354, Met355 |
| Quercetin 3-xyloside | −11.5 | −4.9 | −4.4 | Ile354, Thr279, His440 |
| Kaempferol | −9.2 | −4.0 | −2.7 | Tyr314 |
| Quercetin | −9.1 | −4.2 | −3.2 | Tyr314, Phe273, Gln277 |

Figure 8A:
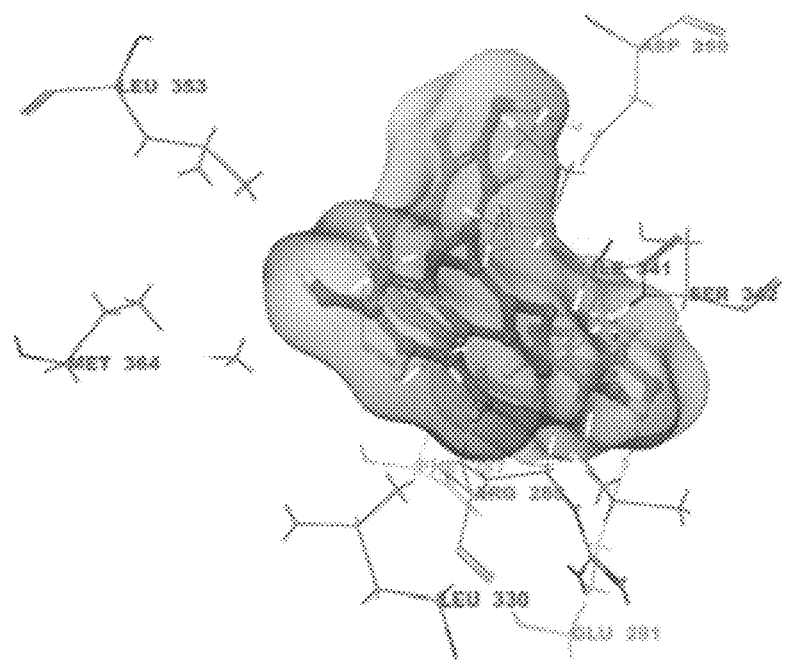
FIGS. 8A and 8B show the molecular docking interaction of isoquercetin with the ligand binding domain of PPARγ.
Figure 8B:
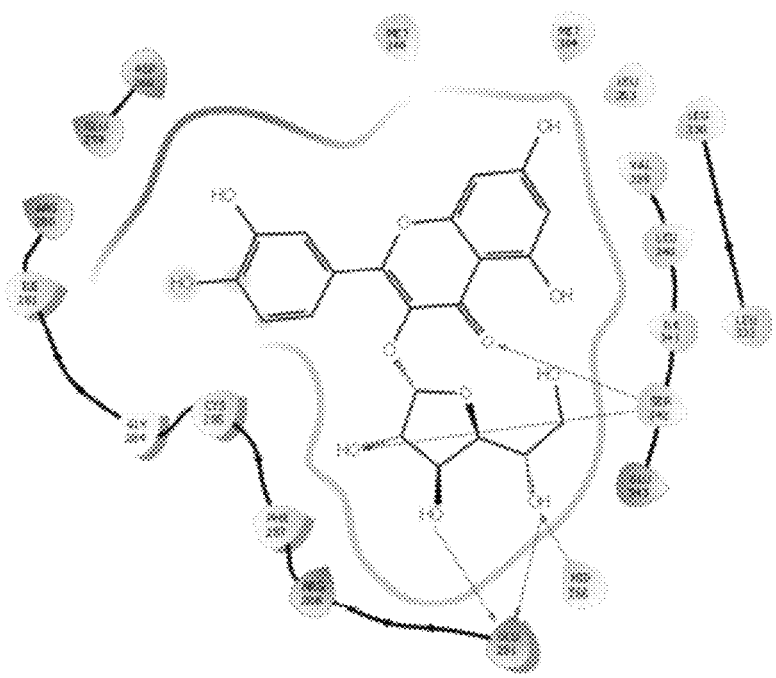
Figure 9A:
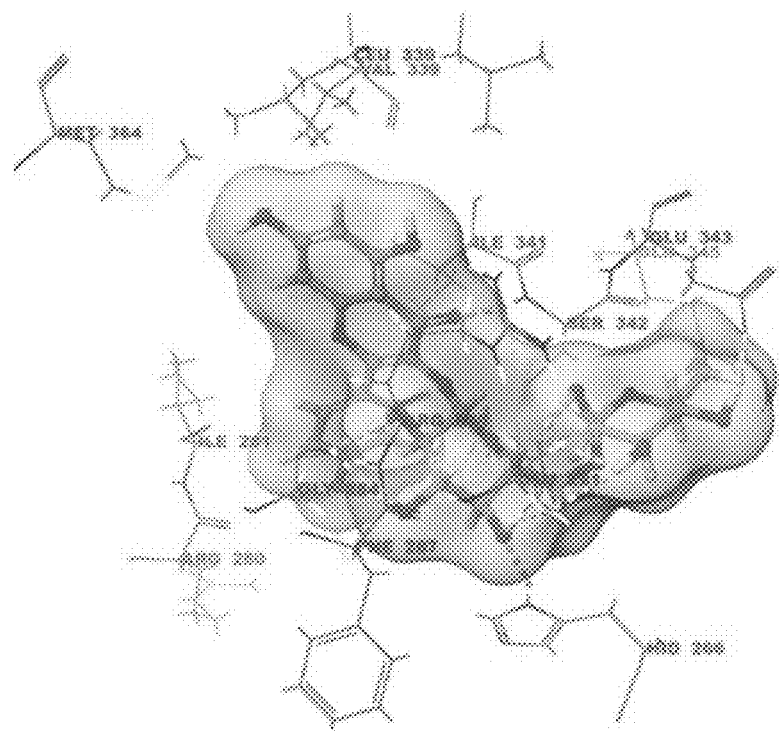
FIGS. 9A and 9B demonstrate the interaction of kaempferol 3-O-rutinoside and the ligand binding domain of PPARγ.
Figure 9B:
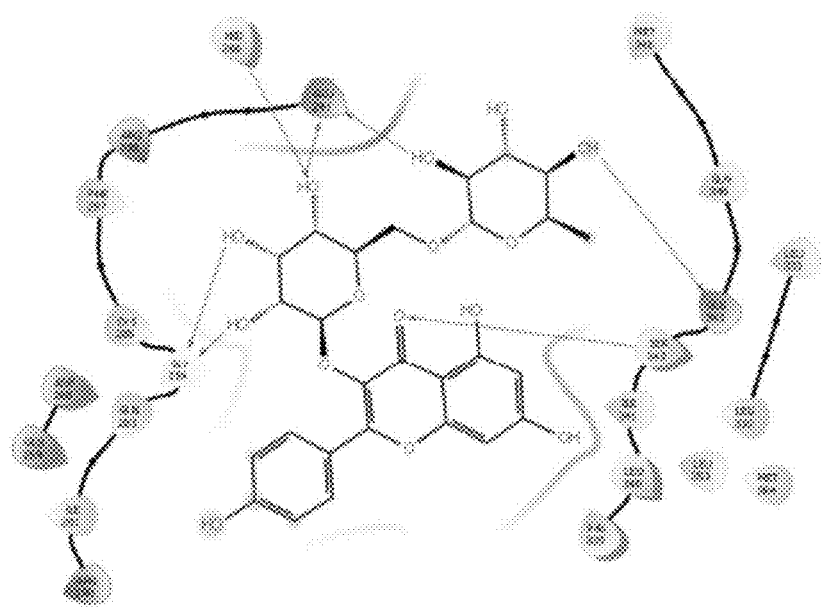

The docking results revealed that isoquercetin and Kaempferol derivatives in the composition had strong binding efficiencies with the LBD of PPARγ (FIGS. 8 and 9). Kaempferol 3-O-rutinoside, quercetin 3-O-galactoside and quercetin 3-O-xyloside were the best fit ligands with Glide score of −11.1, −11.7 and −11.4 respectively (Table 5). Interestingly, two of the polyphenols, isoquercetin and Kaempferol 3-O-rutinoside showed partial agonism having H-bond interaction with Ser342 in the LBD of PPARγ. Furthermore, these molecules interacted with acidic amino acid Glu291 within 3 Å of PPARγ LBD. Except quercetin and its derivative quercetin 3-xyloside none of the composition's ligands showed any interaction with the residues Tyr327, His449 and His323 from arm I of PPARγ LBD.

TABLE 5

Docking score of polyphenols and PPARγ ligand binding domain

| Ligands | GScore | LipophilicEvdW | HBond | Interactions |
|---|---|---|---|---|
| Isoquercetin | −9.3 | −2.7 | −5.0 | His266, Ser342, Glu291, Gly284, Asp260 |
| Kaempferol 3-rutinoside | −11.1 | −3.5 | −5.8 | His266, Ser342, Glu291, Gly284 |
| Quercetin 3-galactoside | −11.7 | −5.0 | −5.0 | Arg288, Ile326, Leu340, Cys285 |
| Quercetin 3-xyloside | −11.4 | −5.4 | −3.7 | Arg288, Tyr327, His449 |
| Kaempferol | −7.7 | −4.3 | −1.7 | Cys285, Tyr473, Arg288 |
| Quercetin | −9.1 | −4.1 | −2.9 | Tyr327, Leu340, His449 |

The present invention relates to the plant extract composed of bioactive polyphenols which can strongly interact and hence modulate the transcriptional activation of PPARα and γ. The dual agonists of PPARα and γ may attribute to the efficacy of the inventive composition in exerting lipid lowering effect as well as enhancing the insulin sensitivity.

Example 4—Determination of Ferric Ion Reducing Antioxidant Power (FRAP) and Nitric Oxide Scavenging Potentials In Vitro The present invention includes the efficacy evaluation of the composition in free radical scavenging using in vitro studies. The composition is a polyphenol rich preparation having high antioxidant potentials. Our investigation demonstrated the antioxidant capacity of the composition through FRAP and nitric oxide scavenging assays.

In the present investigation, the different concentrations of the inventive composition were prepared from a 10 mg/mL aqueous solution for testing the efficacy in vitro.

Ferrous Ion Reducing Antioxidant Power Assay:

FRAP assay was performed following the method of Benzie and Strain (1996). The FRAP working reagent was prepared by mixing acetate buffer (300 mM, pH 3.6), 10 mM 2,4,6-tripyridyl-s-triazine (TPTZ) in 40 mM HCl and $FeCl_3.6H_2O$, in the ratio of 10:1:1. The assay was performed by adding 0.5 mL of different concentrations of the inventive composition (50-300 µg/mL) into 3 mL of working FRAP reagent. The absorbance was measured at 593 nm. The calibration curve of known $Fe^{2+}$ concentration was prepared using methanol solutions of $FeSO_4.7H_2O$ (50 µM to 2000 µM). The FRAP value of the inventive composition at different concentrations was determined using a standard curve.

Figure 10A:
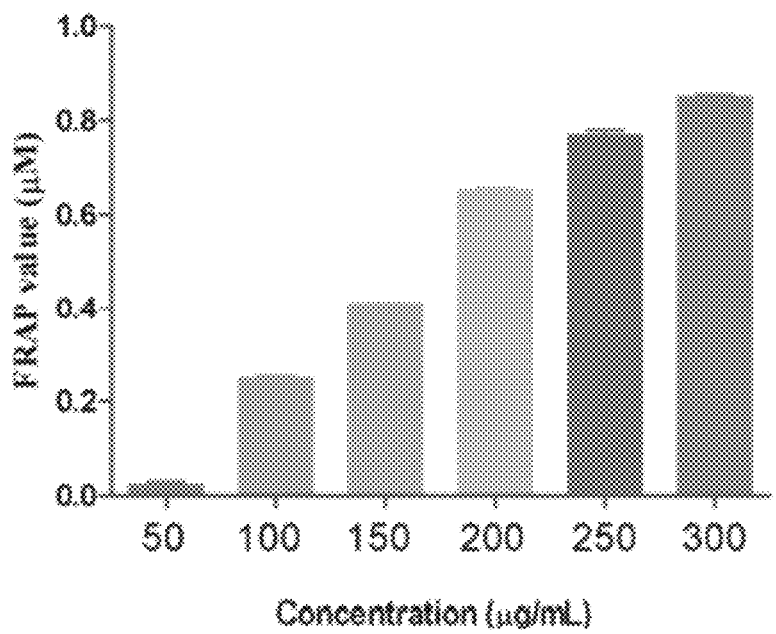
FIG. 10A is a graph showing the ferric ion reducing antioxidant power (FRAP) value of an embodiment of the composition.

FRAP value is an important parameter which determines the antioxidant potentials of any compound. The antioxidants act as reductants reducing a colorless ferric tripyridyl-triazine complex into blue colored ferrous-(2,4,6-tripyridyl-s-triazine) which can be measured colorimetrically at wavelength of 593 nm. In the present investigation, the polyphenol rich composition showed appreciable FRAP values at lower concentration range (50-300 µg/mL). Further, as shown in FIG. 10A, the FRAP value increased in a concentration dependent manner Nitric Oxide Scavenging Assay:

The polyphenol rich extract of the inventive composition was further tested for in vitro nitric oxide (NO) scavenging according to the methods of Panda et al. (2009) with slight modifications. Briefly, a volume of 0.5 mL of 5 mM sodium nitroprusside in phosphate buffered saline was mixed with 1 mL of various concentrations of the inventive composition (10-250 µg/mL) and incubated for 180 min. at 25° C. Control samples without extract were also prepared. After 60 min of incubation an aliquot of reaction mixture was mixed with equal volume of freshly prepared Griess reagent (equal amounts of 1% sulphanilamide in 2.5% phosphoric acid and 0.1% naphthylethylene diamine dihydrochloride in 2.5% phosphoric acid) and transferred to 96 well plate. The absorbance was measured at 570 nm using microplate reader (Thermo Scientific MultiskanEX). At different time points the absorbance was recorded. The percentage nitrite radical scavenging was calculated using the formula:

$$\text{Nitric oxide scavenged (\%)} = \frac{A_{control} - A_{test}}{A_{control}} \times 100$$

Where $A_{control}$=absorbance of control sample and $A_{test}$=absorbance in the presence of the composition.

Nitric oxide is a crucial free radical generated in the cells from L-arginine amino acid. NO worsens the toxicity and adverse conditions when reacts with superoxide radical forming highly reactive peroxynitrite anion (Nagmoti et al.

Figure 10B:
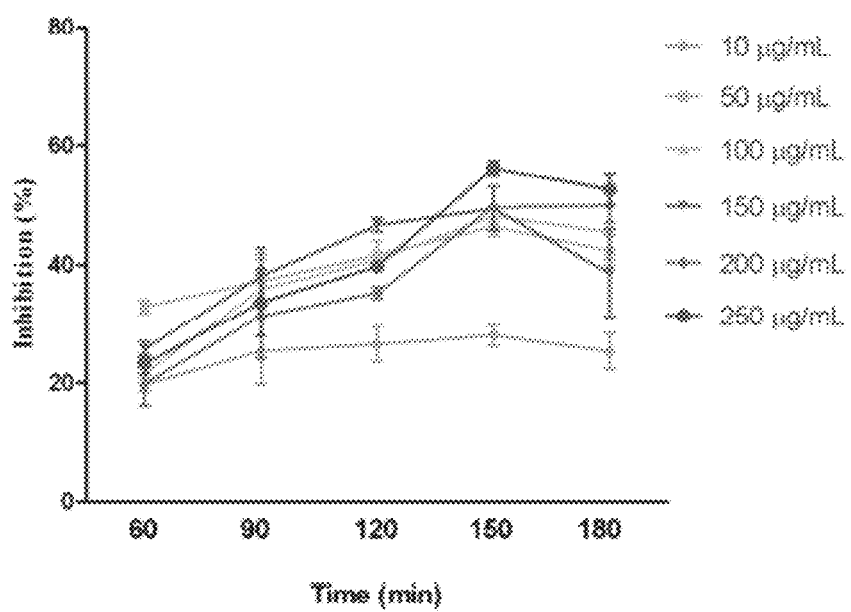
FIG. 10B shows the nitric oxide scavenging activity of an embodiment of the composition.

2011). Use of natural antioxidants is a promising alternative to combat with the oxidative stress associated complications. The composition effectively scavenged nitrite radical in a concentration dependent manner and reached a plateau (FIG. 10B). The IC50 value recorded was 213.3 µg/mL.

Example 5—In Vitro Enzyme Inhibition Studies

Pancreatic Lipase Inhibition Assay:

Pancreatic lipase is secreted from the pancreas and is the primary lipase that is responsible for the uptake of free fatty acids in the intestinal lumen. The ability of the composition to inhibit pancreatic lipase was measured using the method previously reported by Kim et al (2007).

Enzyme buffer: 6 µL porcine pancreatic lipase solution (Sigma-Aldrich) was added in buffer containing 10 mM MOPS (Morpholinepropanesulphonic acid) and 1 mM EDTA, pH 6.8, to 169 µL Tris buffer (100 mM Tris-HCl and 5 mM $CaCl_2$), pH 7.0).

Assay: The reaction mixture contained 20 µL of the composition or standard drug orlistat at the different test concentrations (10, 50 and 100 µg/mL), 175 µL enzyme buffer and 5 µL substrate solution (10 mM p-NPB (p-nitrophenylbutyrate) in dimethyl formamide). The mixture was incubated for 15 min at 37° C. Lipase activity was determined by measuring the hydrolytic conversion of p-NPB to p-nitro phenol at 405 nm using UV-visible spectrophotometer. Inhibition of lipase activity was expressed as the percentage decrease in optical density when porcine pancreatic lipase was incubated with the test samples. Lipase inhibition (%) was calculated according the following formula:

$$\text{Inhibition \%} = 100 - \{B - b/A - a \times 100\}$$

where 'A' is the activity without inhibitor, 'a' is the negative control without inhibitor, 13' is the activity with inhibitor, and 'b' is the negative control with inhibitor. The results were expressed as an average. Inhibition of pancreatic lipase is expressed in terms of percentage.

Figure 11A:
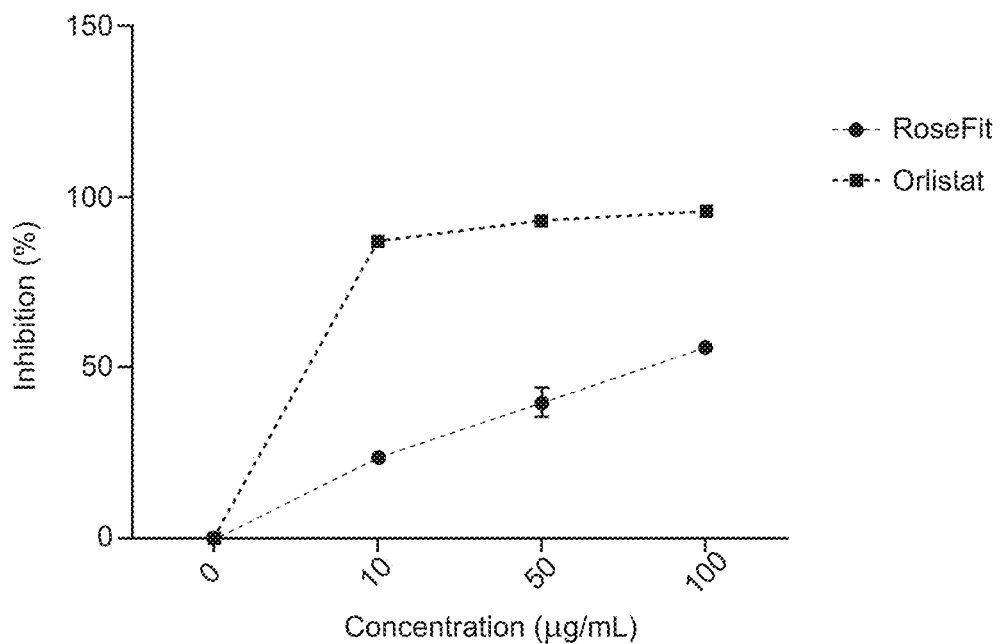
FIG. 11A is a line graph showing the percentage inhibition of pancreatic lipase activity by an embodiment of the composition compared to Orlistat.

As shown in FIG. 11A, appreciable results were obtained with the inventive composition inhibiting the enzyme activity in a concentration dependent manner (IC50=81.4 µg/mL). The inhibitory effects were comparable to standard drug orlistat. Pancreatic lipase is an important enzyme that plays crucial role in dietary lipid absorption. The enzyme secreted by the pancreatic acinar cells, completely hydrolyses the dietary triglycerides in the form of emulsion, into free fatty acids, monoacylglycerols and diacylglycerols. Inhibition of pancreatic lipase is a promising strategy to treat obesity. Orlistat is the only FDA approved anti-obesity drug which works through inhibition of pancreatic lipase. The inventive composition forms an alternative lipase inhibitor which can be effectively promoted for treatment of obesity.

α-Glucosidase Inhibition Assay

The mixture of 20 µL pNPG substrate solution (at concentrations of 0.2 mmol/L, 0.4 mmol/L, 0.8 mmol/L, 1.0 mmol/L, 1.6 mmol/L, and 2.0 mmol/L), 112 µL PBS, and 8 µL OF the inventive composition (0.25-2 µg/mL) were incubated in a 96-well plate at 37° C. for 15 min, followed by the addition of 20 µL of the enzyme solution (1 unit/mL) to each well and 5 min incubation at 37° C. The reaction was terminated by the addition of 80 µL of $Na_2CO_3$ solution (0.2 mol/L) and the OD values were measured at 405 nm.

Figure 11B:
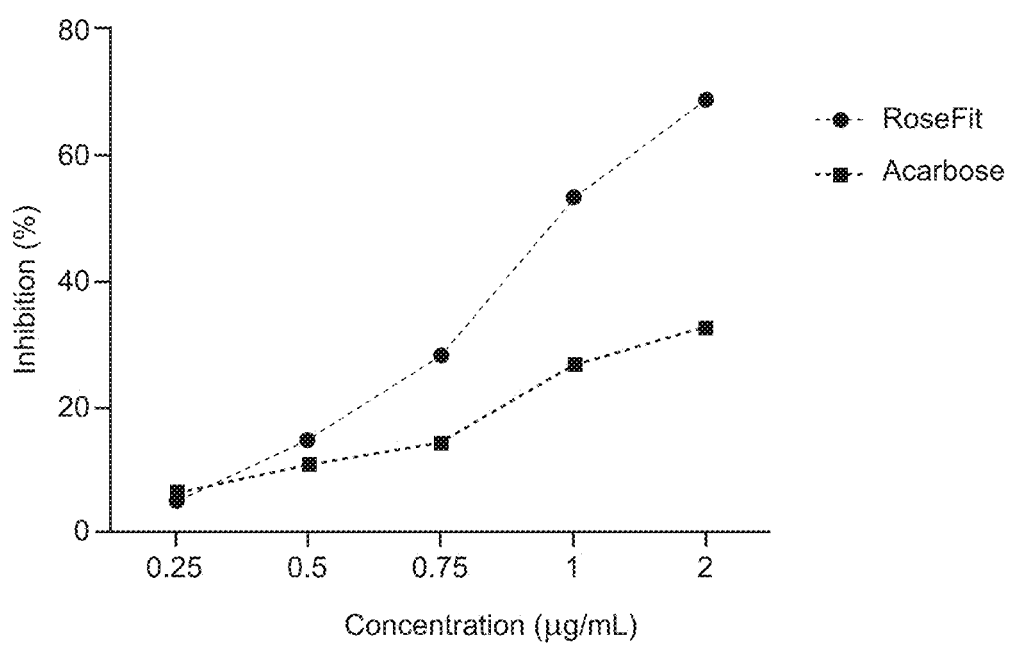
FIG. 11B is line graph showing the percentage inhibition of α-glucosidase enzyme by an embodiment of the composition compared to acarbose.

The IC50 value recorded for the composition was 1.33 µg/mL. The inventive composition exhibited potent inhibitory effects as compared to the standard Acarbose (FIG. 11B).

Example 6—In Vitro Antiadipogenic Activity and Adipocyte Differentiation

The present invention provides methods for evaluating the effect of the composition on adipocyte differentiation using 3T3L1 preadipocytes.

Chemicals and Biochemicals 3-(4,5-Dimethylthiazol-2-yl)-2,5-diphenyltetraolium bromide, Dexamethasone (DXM), bovine pancreatic insulin, 3-isobutyl-1-methylxanthine (IBMX) and Dulbecco's Modified Eagle Medium were purchased from Sigma-Aldrich. The measurement of protein was carried out with an assay kit from Bio-Rad (Mississauga, ON), antibodies for PPARγ and C/EBPb, and β-actin (Santa Cruz CA).

MTT Assay

MTT assay was carried out by adopting the protocol described by Lau et al. (2004). Briefly, 3T3-L1 mouse adipocytes ($5 \times 10^3$/well) were seeded in 96-well plates, after 16 hr of incubation, cells were treated with different concentrations (0.2-2 mg/mL) of the composition and incubated at 37° C. in 5% $CO_2$ and 95% air. After 24 h, medium was replaced with 20 µL aliquot of 3-(4,5-Dimethylthiazol-2-yl)-2,5-diphenyltetraolium bromide (MTT, a yellow tetrazole; 5 mg/ml in PBS) dye solution for 4 h at 37° C. The supernatant was decanted carefully, 100 µl of DMSO was added and mixed, and the absorbance was read at 563 nm to determine the formazan concentration which is proportional to the number of live cells.

Cell Culture and Adipocyte Differentiation

3T3-L1 mouse adipocytes were grown in DMEM containing 10% FBS and 100 U/ml penicillin-streptomycin at 37° C. with humidified air containing 5% $CO_2$ until confluent at 100% and were then maintained in the same medium for an additional 2 days. Differentiation was induced 2 days post-confluence (day 0 of differentiation) by adding 0.5 mM IBMX, 1 mM dexamethasone, and 5 mg/mL insulin in DMEM with 10% FBS (MDI for 2 days. After 2 days of incubation, culture medium was changed to fresh DMEM containing 10% FBS and 5 mg/mL insulin and incubated for another two days (designated as day 4), subsequently the cells were maintained in DMEM supplemented with 10% FBS by changing the medium for every 2 days for six days at which time more than 90% of the cells were mature adipocytes with accumulated fat droplets. The inventive composition was added into the medium on Day 4 during 8-day differentiation.

Oil Red O Staining

Intracellular lipid accumulation was measured using Oil Red O staining. The Oil Red O working solution was prepared as described by Ramirez-Zacarias et al. (16). The 3T3-L1 cells ($0.2 \times 10^6$/well) were cultured in 6-well plates and treated with the composition at a dose of 250 and 500 µg in differentiation medium (MDI) every 2 days during the 10-day differentiation period. After differentiation, cells were washed with PBS, fixed with 10% formaldehyde then stained for 1 hr with a filtered solution of 60% Oil Red O in 100% aqueous 2-isopropanol. To quantify the intracellular lipids, the stained lipid droplets were dissolved in isopropanol (3 mL per well). The extracted dye was transferred into a 96-well plate and the absorbance was read with a MultiscanEx microplate reader (Thermofischer) at 500 nm.

Western Blotting

After 10-days differentiation in the presence of the composition, 3T3-L1 adipocytes were collected and lysed in ice-cold RIPA lysis buffer for 30 minutes. Protein concentrations were determined using a Bradford reagent. Equal amounts of protein for each sample was loaded and separated on a 10% SDS-PAGE. After electrophoretic separation, the proteins were transferred to a nitrocellulose membrane using a semi-dry transfer and blocked with 5% skim milk for 1 hr at room temperature, and incubated with primary antibodies at 4° C. overnight. The nitrocellulose filters were then incubated with horseradish peroxidase conjugated secondary antibody at room temperature for 3 hrs Immunoreactive proteins were detected using the chemiluminescent ECL assay and quantified using the Molecular Imager software (Bio-Rad). C/EBPβ expression was determined 2 days after the induction of cell differentiation in the presence or absence of the indicated concentrations of the inventive composition. The expression of each protein was present as fold of the loading control, β-actin.

Figure 12:
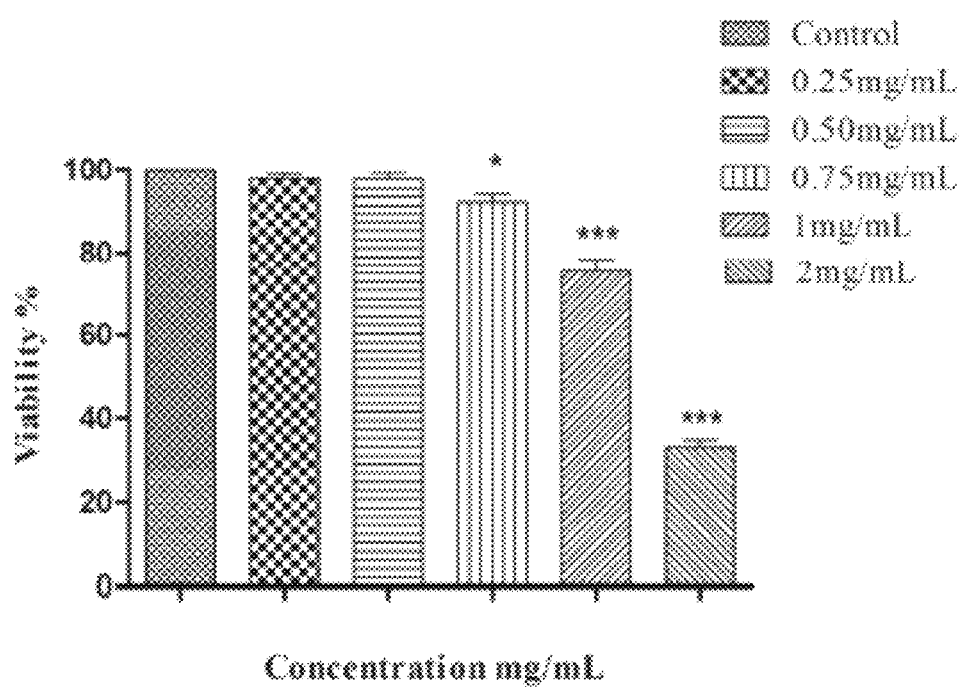
FIG. 12 is a bar graph showing the effect of an embodiment of the composition on the viability of 3T3L1 cells.

The viability of 3T3-L1 cells after exposure to different concentrations (0.25-2 mg/mL) of the composition was measured by MTT assay (FIG. 12). MTT assay results revealed the composition showed little cytotoxicity in 3T3-L1 adipocytes up to the concentration of 1 mg/mL. Treatment with 1 and 2 mg/mL of the composition showed decreased cell viability by approximately 34.52% and 66.89% respectively. However, no inhibitory effects on cell viability were observed in cells treated with up to 0.5 mg/ml of the composition.

Figure 13A:
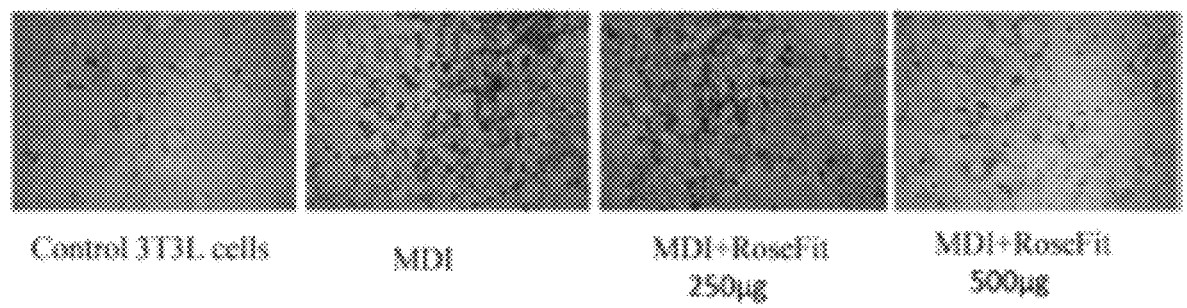
FIG. 13A shows the images of Oil Red O staining of differentiated 3T3-L1 adipocytes in the absence or presence of an embodiment of the composition (250 μg/mL and 500 μg/mL).
Figure 13B:
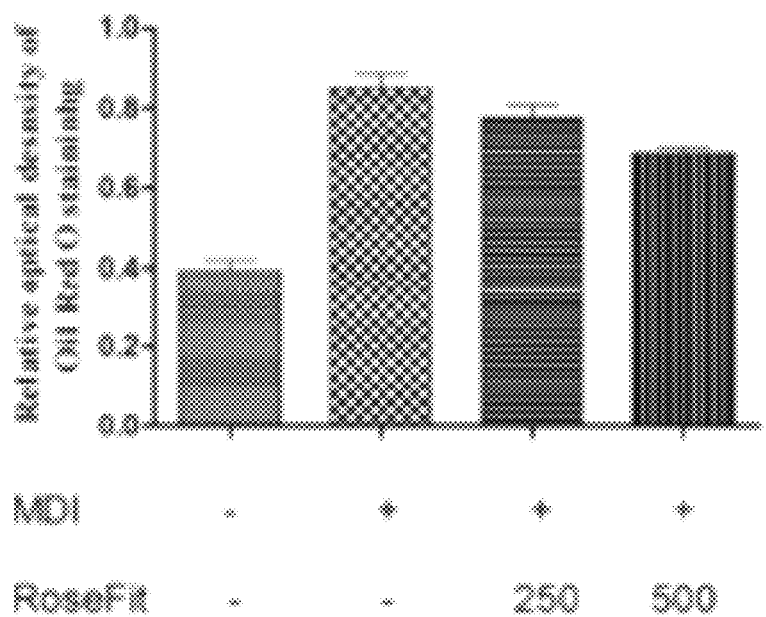
FIG. 13B is a bar graph showing the effect of an embodiment of the composition on lipid accumulation in 3T3-L1 cells.

Further, adipocyte differentiation was induced with the differentiation medium (MDI cocktail) supplemented with composition at a dose of 0.25-0.5 mg/ml for every 2 days until fully differentiated. Lipid accumulations were assessed by Oil red O staining. As shown in FIGS. 13A and 13B, 0.5 mg/mL of the composition suppressed lipid accumulation in 3T3-L1 adipocytes at levels that were statistically significant ($p<0.05$), showing the composition inhibits adipogenesis in 3T3-L1 cells.

Figure 14:
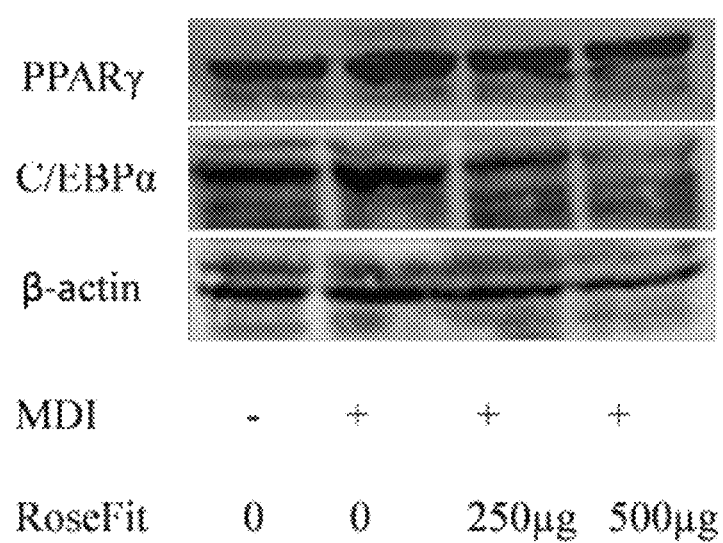
FIG. 14 shows a Western blot analysis of 3T3-L1 adipocytes treated with an embodiment of the composition.

To examine the anti-adipogenic mechanism, the effect of the composition on protein levels of PPARγ and C/EBPα were investigated. Fully differentiated 3T3-L1 cells were exposed for 6 days at the concentrations of 0.25-0.50 mg/mL of the composition followed by the extraction of the total proteins for western blot analysis. Western blot results clearly demonstrated that the composition resulted in dose dependent suppression of protein levels of PPARγ and C/EBPα (FIG. 14).

Example 7—In Vitro Antioxidant Assays

DPPH Scavenging Activity

A rapid, simple and inexpensive method to measure antioxidant/free radical scavenging power involves the use of the free radical, 2,2-Diphenyl-1-picrylhydrazyl (DPPH) (Qian and Nihorimbere, 2004; Olaleye et al., 2004). DPPH is widely used to test the ability of compounds to act as free radical scavengers or hydrogen donors, and to evaluate antioxidant activity of foods. The odd electron in the DPPH free radical gives a strong absorption maximum at 517 nm and is purple in color. The color turns from purple to yellow as the molar absorptivity of the DPPH radical at 517 nm reduces from 9660 to 1640 when the odd electron of DPPH radical becomes paired with hydrogen from a free radical scavenging antioxidant to form the reduced DPPH-H. The resulting decolorization is stoichiometric with respect to number of electrons captured.

Method

The free radical scavenging capacity of the composition was determined using DPPH scavenging assay (Braca et al. 2001). DPPH solution was prepared in 95% methanol. Freshly prepared DPPH solution was taken in test tubes and different concentration of the composition (20-100 μg/mL) were added and incubated for 20 min. The absorbance was read at 517 nm using a spectrophotometer. Blank was prepared containing the same volume of reaction mixture without any test samples. The percentage of scavenging was calculated using formula:

% Scavenging=$A_c$-$A_s$/$A_c$×100

Where $A_C$ was the absorbance of the control (blank without extract) and $A_s$ was the absorbance in the presence of the extract.

Result

Figure 15A:
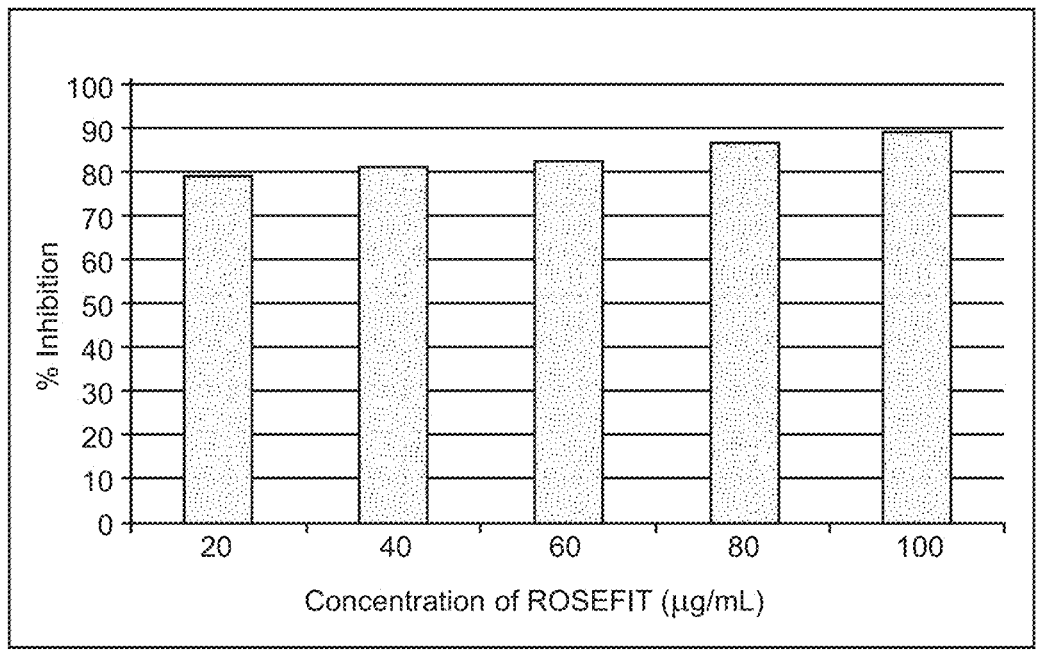
FIGS. 15A and 15B show inhibition of DPPH radical by an embodiment of the composition (FIG. 15A) and ascorbic acid (FIG. 15B).
Figure 15B:
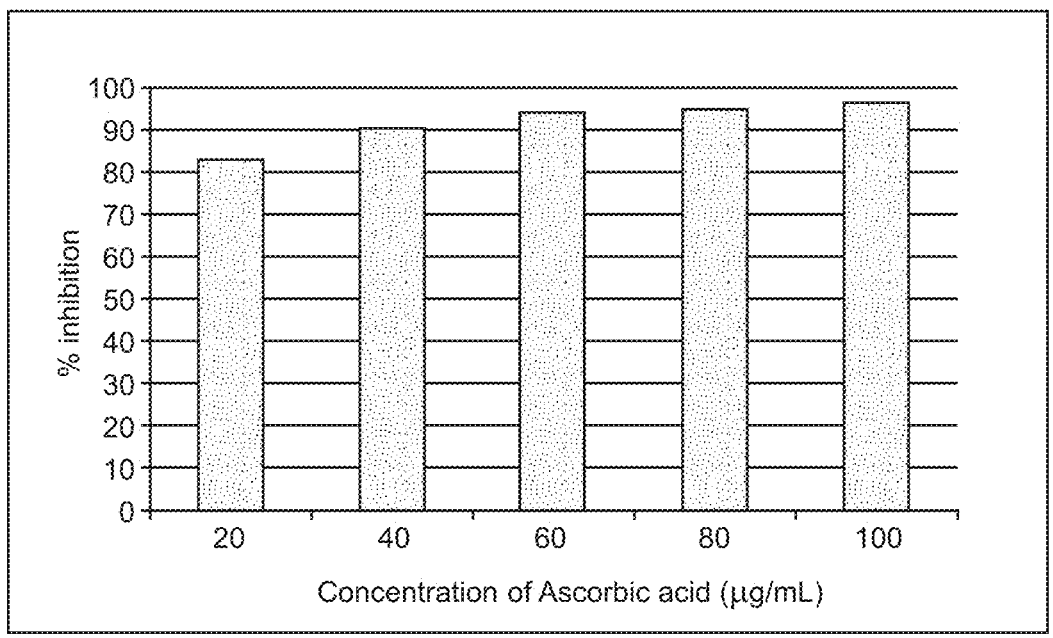

FIGS. 15A and 15B show the concentration dependent increase in DPPH radical scavenging activity of the composition compared to ascorbic acid. The composition was effective in a dose dependent manner scavenging free radical. It was observed that extract had maximum activity of 89.09% at 100 μg/ml concentration, which was comparable with ascorbic acid (96.71%).

Superoxide Anion Scavenging Activity

Superoxide anion scavenging activity of the composition was carried out by the procedure described by the protocol of McCord and Fridovich (1969). Briefly, the reaction mixture 3 ml containing EDTA (6 mM), 3 μg NaCN; riboflavin (2 μM) NBT (50 μM); $KH_2PO_4$—$Na_2HPO_4$ buffer (67 mM, pH 7.8) and various concentrations of composition (20-100 μg/ml) were taken in different tubes and tubes were illuminated under incandescent lamp for 15 minutes. The optical density (O.D) was read at 530 nm. The inhibition of super oxide radical generation was determined by comparing the absorbance values of the control with that of treatments. Percent scavenging was calculated as follows:

$$\% \text{ Scavenging} = \frac{A560_{Control} - A560_{Test}}{A560_{Control}} \times 100$$

Figure 16:
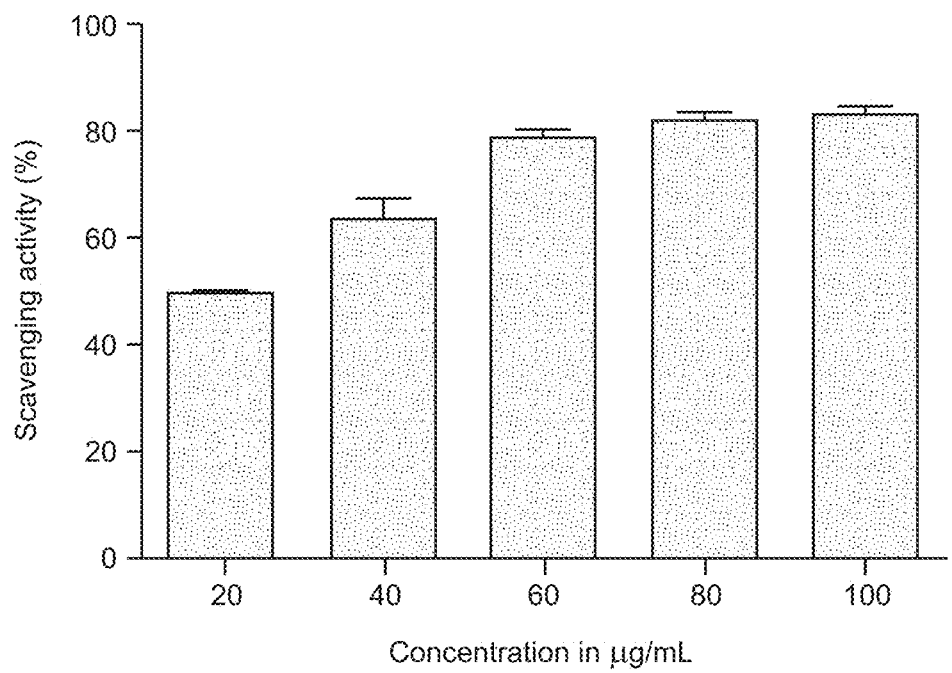
FIG. 16 shows the superoxide scavenging activity of an embodiment of the composition.

The percent inhibition of superoxide anion scavenging activity of the composition are presented in FIG. 16. The superoxide radical scavenging activity of the composition was found to be dose dependent. Interestingly, the composition showed the highest inhibitory activity of 82.8% at the concentration of 100 μg/ml. Superoxide anions are produced from molecular oxygen due to the enzyme systems in auto-oxidation reactions and by non-enzymic electron transfer (Anitha et al., 2012) and very detrimental to cellular components.

Reducing Power Assay

The reducing power of the composition and butylated hydroxytoluene (BHT) was measured using the methods reported by Oyaizu et al. (1986). Briefly, 1ml of the composition at different concentrations (20-100 μg/ml), 2.5 mL of phosphate buffer (0.2 mol/L, pH 6.6) and 1.0 ml potassium ferricyanide (1%, w/v) were mixed and incubated at 50° C. for 20 min. Subsequently, to terminate the reaction 2 ml of trichloroacetic acid (10%, w/v) and 1.2 ml ferric chloride (0.1%, w/v) were added to the reaction mixture. The absorbance was measured at 700 nm using deionized water as a blank.

Figure 17:
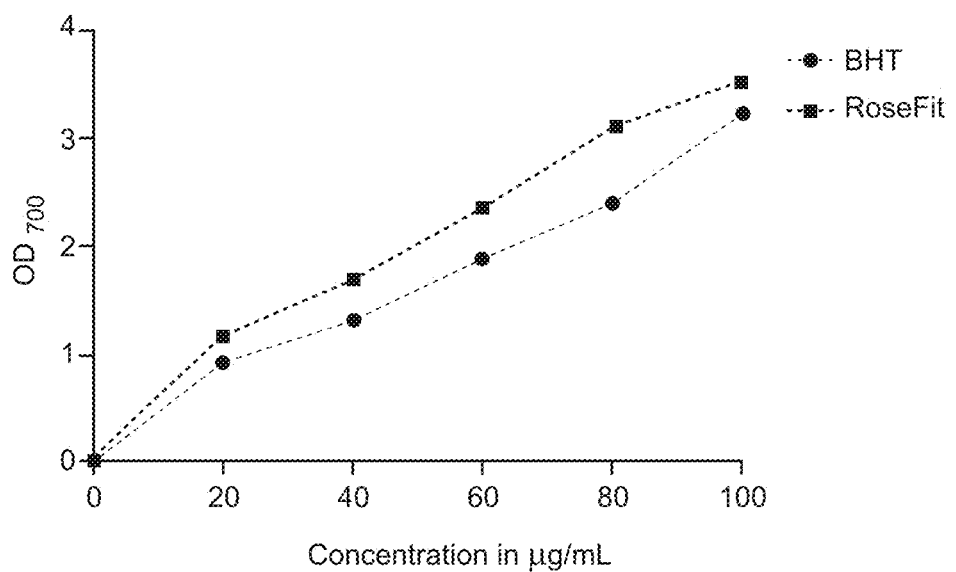
FIG. 17 shows the reducing power of an embodiment of the composition compared to butylated hydroxytoluene.

The ferric reducing assay measures the ability of an antioxidant to reduce a reactive oxygen species against that species' oxidative power (Saklani et al., 2011). This is important to make the reactive oxygen species more stable and unreactive. The reducing capacity of the composition was compared with standard BHT (FIG. 17). An increase in absorbance at 700 nm indicates the reducing power of the sample. The composition showed higher reducing power than BHT. Reducing power is related to the presence of reductones which convert ferricyanide complex ($Fe^{3+}$) to ferrous ($Fe^{2+}$) in presence of antioxidants.

REFERENCES

Benzie F F, Strain J J. The ferric reducing ability of plasma (FRAP) as a measure of antioxidant power: the FRAP assay. Analytical Biochemistry 1996; 239(1): 70-76.

Chang C, Yang M, Wen H, Chern J. Estimation of total flavonoid content in propolis by two complementary colorimetric methods. Journal of Food and Drug Analysis 2002; 10: 178-182.

Giusti M M, Rodnguez-Saona L E, Wrolstad R E. Molar absorptivity and color characteristics of acylated and non-acylated pelargonidin-based anthocyanins. Journal of Agricultural Food Chemistry 1999; 47: 4631-4637.

Harmon G S, Lam M T, Glass C K. PPARs and lipid ligands in inflammation and metabolism. Chemical reviews 2011; 111: 6321-6340.

Hasani-Ranjbar S, Jouyandeh Z, Abdollahi M. A systematic review of anti-obesity medicinal plants—an update. Journal of Diabetes and Metabolic Disorders 2013; 12:28.

Hasani-Ranjbar S, Nayebi N, Larijani B, Abdollahi M. A systematic review of the efficacy and safety of Teucrium species: from anti-oxidant to anti-diabetic effects. International Journal of Pharmacology 2010; 6: 315-25.

Hasani-Ranjbar S, Nayebi N, Larijani B, Abdollahi M. A systematic review of the efficacy and safety of herbal medicines used in the treatment of obesity. World Journal of Gastroenterology 2009; 15: 3073-85.

Hasani-Ranjbar S, Nayebi N, Moradi L, Mehri A, Larijani B, Abdollahi M. The efficacy and safety of herbal medicines used in the treatment of hyperlipidemia; a systematic review. Current Pharmaceutical Design 2010; 16: 2935-47.

Joint FAO/WHO Expert Consultation. WHO Technical Report Series 916: Diet, Nutrition and the Prevention of Chronic Diseases; World Health Organization: Geneva, Switzerland, 2003.

Kim G W, Lin J E, Blomain E S, Waldman S A. Anti-obesity pharmacotherapy: new drugs and emerging targets. Clinical Pharmacology & Therapeutics 2014; 95: 53-66.

Kim J H, Kim H J, Park H W, Youn S H, Choi D Y, Shin C S. Development of inhibitors against lipase and α-glucosidase from derivatives of monascus pigment. FEMS Microbiology Letters 2007; 276(1): 93-98.

Lau C B, Ho C Y, Kim C F, Leung K N, Fung K P, Tse T F, Chan H H, Chow M S. Cytotoxic activities of Coriolus versicolor (Yunzhi) extract on human leukemia and lymphoma cells by induction of apoptosis. Life Sciences 2004; 7: 797-808.

Nagmoti D M, Khatri D K, Juvekar P R, Juvekar A R. Antioxidant activity and free radical-scavenging potential of Pithecellobium dulce Benth seed extracts. Free Radical and Antioxidants 2011; 2(2): 37-43.

Newman D J, Cragg G M. Natural products as sources of new drugs over the 30 years from 1981 to 2010. Journal of Natural Products 2012; 75: 311-35.

Panda B N, Raj A B, Shrivastava N R, Prathani A R. The evaluation of nitric oxide scavenging activity of Acalypha indica Linn Root. Asian Journal Research Chemistry 2009; 2(2): 148-150.

Popkin B M. The nutrition transition and obesity in the developing world. Journal of Nutrition 2001; 131: 871S-873S.

Rucker D, Padwal R, Li S K, Curioni C, Lau D C W. Long term pharmacotherapy for obesity and overweight: update meta-analysis. BMJ 2007; 335: 1194-9.

Singleton V L, Orthofer R, Lamuela-Raventós R M. Analysis of total phenols and other oxidation substrates and antioxidants by means of Folin-Ciocalteu reagent. Methods in Enzymology 1999; 299: 152-178.

Wong C P, Kaneda T, Morita H. Plant natural products as an anti-lipid droplets accumulation agent. Journal of Natural Medicines 2014; 68: 253-66.

World Cancer Research Fund and American Institute for Cancer Research. Food, Nutrition, Physical Activity, and the Prevention of Cancer: a Global Perspective; American Institute for Cancer Research: Washington, DC, USA, 2007.

Zieleniak A, Wojcik M, Wozniak L A. Structure and physiological functions of the human peroxisome proliferator-activated receptor gamma Archivum immunologiae et therapiae experimentalis 2008; 56: 331-345.

The invention claimed is:

1. A method of reducing body weight, comprising administering to an obese subject an effective amount of a composition comprising a supercritical fluid red rose petal extract, wherein said extract comprises about 3.50 w/w % isoquercetin and about 0.30 w/w % quercetin, and wherein administering said composition reduces body weight in said subject.

2. The method of claim 1, wherein said extract comprises about 66.0 w/w % polyphenols, about 9.5 w/w % flavonoids, and about 2.7 w/w % anthocyanins.

3. The method of claim 1, wherein said extract comprises 66.44±3.09 w/w % polyphenols, 9.47±1.23 w/w % flavonoids, and 2.73±0.38 w/w % anthocyanins.

4. The method of claim 1, wherein said extract comprises about 0.30 w/w % rutin.

5. The method of claim 1, wherein said extract comprises 3.48±0.11 w/w % isoquercetin, 0.25±0.28 w/w % quercetin, 0.33±0.02 w/w % rutin, or combinations thereof.

6. The method of claim 1, wherein said extract comprises at least one phenolic acid.

7. The method claim 1, wherein said extract comprises about 0.30 w/w % ethyl gallate, about 1.90 w/w % ellagic acid, about 0.02 w/w % methyl gallate, about 0.10 w/w % catechin, about 1.40 w/w % gallic acid, about 0.10 w/w % 3,4-dihydroxy benzoic acid, or combinations thereof.

8. The method of claim 1, wherein said extract comprises 0.28±0.04 w/w % ethyl gallate, 1.85±0.33 w/w % ellagic acid, 0.02±0.003 w/w % methyl gallate, 0.11±0.008 w/w % catechin, 1.41±0.04 w/w % gallic acid, 0.09±0.01 w/w % 3,4-dihydroxy benzoic acid, or combinations thereof.

9. The method of claim 1, wherein said extract comprises at least one chlorogenic acid.

10. The method of claim 1, wherein said extract comprises 0.00046±0.0001 w/w % 3-O-caffeoylquinic acid (3-CQA), 0.0114±0.006 w/w % 5-O-Caffeoylquinic acid (5-CQA), 0.0104±0.004 w/w % 4-O-Caffeoylquinic acid (4-CQA), 0.022±0.008 w/w % 3,4 Di-O-caffeoylquinic acid (3,4-DiCQA), 0.388±0.14 w/w % 3,5 Di-O-caffeoylquinic acid (3,5-DiCQA), and 0.0823±0.01 w/w % 4,5 Di-O-caffeoylquinic acid (4,5-DiCQA), or combinations thereof.

11. The method of claim 1, wherein said extract comprises 3.5 w/w % isoquercetin, 1.8-2.0 w/w % ellagic acid, 1.0-1.5 w/w % gallic acid, 0.3-0.35 w/w % rutin, 0.25 w/w % quercetin, 0.1 w/w % catechins, or combinations thereof.

12. The method of claim 1, wherein said composition inhibits pancreatic lipase.

13. The method of claim 1, wherein said composition has an IC50 for pancreatic lipase of about 81.4 μg/Ml.

14. The method of claim 1, wherein said composition inhibits α-glucosidase.

15. The method of claim 1, wherein said composition has an IC50 for α-glucosidase of about 1.33 μg/Ml.

16. The method of claim 1, wherein said composition has an IC50 for nitric oxide scavenging activity of about 213.3 μg/Ml.

17. The method of claim 1, wherein said composition has a radical scavenging activity of about 89% at a concentration of 100 μg/ml as determined by DPPH assay.

18. The method of claim 1, wherein said composition has a superoxide scavenging activity of about 82.8% at 100 μg/ml.

19. The method of claim 1, wherein said supercritical fluid rose petal extract is supercritical fluid *Rosa multiflora* rose petal extract.

20. The method of claim 1, wherein said subject has a metabolic disorder selected from the group consisting of prediabetes, diabetes, type 1 diabetes, type 2 diabetes, dyslipidemia, hyperglycemia, and combinations thereof.

21. The method of claim 1, wherein said composition is administered orally, buccally, sub-lingually, parenterally, intravenously, intravaginally, rectally, by inhalation, or combinations thereof.

22. The method of claim 1, wherein said composition is in a form selected from the group consisting of a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, injection, and combinations thereof.

23. The method of claim 1, wherein said supercritical fluid is carbon dioxide.

* * * * *